US011037293B2

(12) United States Patent
Ariga et al.

(10) Patent No.: US 11,037,293 B2
(45) Date of Patent: Jun. 15, 2021

(54) CELL OBSERVATION SYSTEM

(71) Applicant: OLYMPUS CORPORATION, Tokyo (JP)

(72) Inventors: Naohiro Ariga, Tokyo (JP); Shintaro Takahashi, Tokyo (JP); Yohei Tanikawa, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 29 days.

(21) Appl. No.: 16/458,397

(22) Filed: Jul. 1, 2019

(65) Prior Publication Data

US 2019/0333215 A1 Oct. 31, 2019

Related U.S. Application Data

(63) Continuation of application No. PCT/JP2017/045775, filed on Dec. 20, 2017.

(30) Foreign Application Priority Data

Jan. 6, 2017 (JP) .............................. JP2017-000814
Jun. 14, 2017 (JP) .............................. JP2017-116788

(51) Int. Cl.
*G06T 7/00* (2017.01)
*G01N 33/483* (2006.01)
*G06F 17/18* (2006.01)

(52) U.S. Cl.
CPC ....... *G06T 7/0012* (2013.01); *G01N 33/4833* (2013.01); *G06F 17/18* (2013.01); *G06T 2207/30024* (2013.01)

(58) Field of Classification Search
CPC .. C12M 1/00; C12M 1/34; C12Q 1/02; G01N 33/4833; G06T 2207/10056;
(Continued)

(56) References Cited

U.S. PATENT DOCUMENTS

2003/0040031 A1* 2/2003 Kim ....................... B82Y 30/00
435/29
2003/0134269 A1* 7/2003 Hirai ................... G01N 33/5005
435/4
(Continued)

FOREIGN PATENT DOCUMENTS

EP 3211469 A1 8/2017
EP 3279713 A1 2/2018
(Continued)

OTHER PUBLICATIONS

International Search Report dated Mar. 20, 2018 issued in PCT/JP2017/045775.
(Continued)

*Primary Examiner* — Ian L Lemieux
(74) *Attorney, Agent, or Firm* — Scully, Scott, Murphy & Presser, P.C.

(57) ABSTRACT

A cell observation system includes an imaging element that acquires images of the inside of a culture container in which cells are cultured, the imaging element acquiring the images over time; a computer configured to: quantitatively analyze a culture state of the cells cultured in the culture container on the basis of each of the images acquired by the imaging element; and statistically analyze the quantitatively analyzed data; and a display that displays statistical analysis results in the culture container within a plurality of subculture periods obtained by the computer in a manner allowing comparison of the statistical analysis results.

5 Claims, 26 Drawing Sheets

(58) Field of Classification Search
CPC ......... G06T 2207/30024; G06T 7/0012; G06T 7/0016; G06F 17/18
See application file for complete search history.

(56) References Cited

U.S. PATENT DOCUMENTS

| | | | |
|---|---|---|---|
| 2006/0127370 A1* | 6/2006 | Niwa | C12N 5/0606 424/93.7 |
| 2008/0032321 A1* | 2/2008 | Ginty | G06T 7/143 435/15 |
| 2012/0013727 A1 | 1/2012 | Breniman et al. | |
| 2012/0269781 A1* | 10/2012 | Ra | A61P 17/14 424/93.7 |
| 2012/0295348 A1* | 11/2012 | Nam | A61K 35/30 435/368 |
| 2015/0159141 A1* | 6/2015 | Lin | G01N 33/5067 435/32 |
| 2016/0025612 A1* | 1/2016 | Kuninori | G01N 15/1463 382/133 |
| 2017/0044481 A1 | 2/2017 | Kawano et al. | |
| 2017/0166855 A1* | 6/2017 | Cahan | C12M 41/46 |
| 2017/0204359 A1* | 7/2017 | Ando | G02B 21/365 |
| 2017/0261732 A1 | 9/2017 | Takahashi et al. | |
| 2017/0355949 A1 | 12/2017 | Hirata et al. | |
| 2017/0360955 A1* | 12/2017 | Janssen | A61K 51/1018 |
| 2018/0087020 A1* | 3/2018 | Blanchard | C12M 33/00 |
| 2018/0346956 A1 | 12/2018 | Moriwaki et al. | |
| 2019/0078047 A1* | 3/2019 | Ando | G02B 21/367 |
| 2019/0244349 A1 | 8/2019 | Senda et al. | |
| 2019/0331581 A1* | 10/2019 | Ikehata | C12M 41/32 |
| 2019/0333215 A1* | 10/2019 | Ariga | G06T 7/0012 |
| 2020/0101157 A1* | 4/2020 | Cappellini | A61P 7/00 |

FOREIGN PATENT DOCUMENTS

| | | |
|---|---|---|
| JP | 2002-218995 A | 8/2002 |
| JP | 2015-210212 A | 11/2015 |
| WO | 2006/095896 A | 9/2006 |
| WO | WO 2011/021391 A1 | 2/2011 |
| WO | WO 2015/174356 A1 | 11/2015 |
| WO | WO 2016/158780 A1 | 10/2016 |
| WO | WO 2016/158782 A1 | 10/2016 |

OTHER PUBLICATIONS

U.S. Appl. No. 16/048,792, filed Jul. 30, 2018.
Office Action dated Jan. 30, 2020 received in U.S. Appl. No. 16/048,792.
Vlachynska, A. et al., "Automatic Image-Based Method for Quantitative Analysis of Photosynthetic Cell Cultures", Pervasive: International Conference on Pervasive Computing; [Lecture Notes in Computer Science: Lect. Notes Computer], pp. 402-413.
Extended Supplementary European Search Report dated Sep. 22, 2020 in European Patent Application No. 17 88 9817.7.

* cited by examiner

CELL OBSERVATION SYSTEM

CROSS-REFERENCE TO RELATED APPLICATIONS

This is a continuation of International Application PCT/JP2017/045775 which is hereby incorporated by reference herein in its entirety.

This application claims the benefit of Japanese Patent Applications No. 2017-000814 and No. 2017-116788, the content of which are incorporated herein by reference.

TECHNICAL FIELD

The present invention relates to a cell observation system.

BACKGROUND ART

Conventionally, in the culturing of cells, every time the cells become confluent, the steps of removing a culture container from an incubator, detaching the cells from the culture container and diluting the cells, and seeding and culturing in a new culture container, that is, subculturing, are repeated. Normally, when cultured cells are repeatedly subcultured many times, degradation such as a decrease in proliferative capacity occurs, and cells degraded in such a way may affect the test results.

Therefore, it is desirable that the cells to be used for a test have a stable quality, and it is desirable that there be some indicator for evaluating the quality. For example, a cultured cell evaluation apparatus described in PTL 1 evaluates cell deterioration by classifying cells using the morphological characteristics of cells as an index.

CITATION LIST

Patent Literature

{PTL 1}
PCT International Publication No. 2011/021391WO

SUMMARY OF INVENTION

One aspect of the present invention is a cell observation system including an imaging element that acquires images of the inside of a culture container in which cells are cultured, the imaging element acquiring the images over time; a computer configured to: quantitatively analyze a culture state of the cells cultured in the culture container on the basis of each of the images acquired by the imaging element; and statistically analyze the quantitatively analyzed data; and a display that displays statistical analysis results in the culture container within a plurality of subculture periods obtained by the computer in a manner allowing comparison of the statistical analysis results.

BRIEF DESCRIPTION OF DRAWINGS

FIG. 22 illustrates information illustrating a culture state in which the blank periods in FIG. 21 have been filled in.

DESCRIPTION OF EMBODIMENTS

First Embodiment

A cell observation system according to a first embodiment of the present invention will be described below with reference to the drawings.

Figure 1:
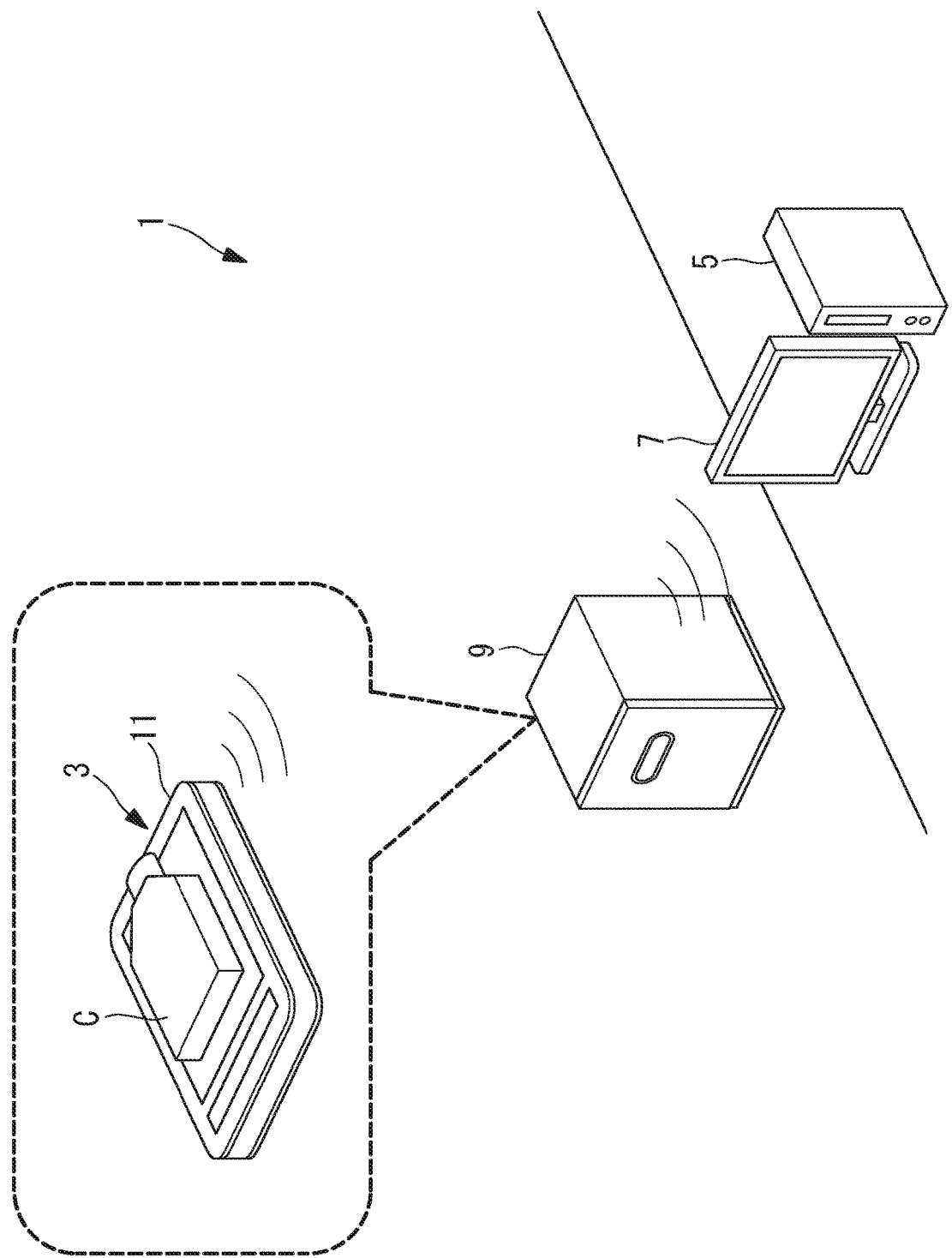
FIG. 1 is a schematic configuration diagram illustrating a cell observation system according to a first embodiment of the present invention.

As illustrated in FIG. 1, a cell observation system 1 according to the present embodiment includes a culture observation apparatus (image acquisition unit) 3 that can acquire images over time of cells A being cultured, a personal computer (PC) main body 5 that processes images obtained by the culture observation apparatus 3, and a monitor (display unit) 7 that displays images acquired by the culture observation apparatus 3, a processing result obtained by processing the images by the PC main body 5, and the like. Reference sign 9 denotes an incubator.

Figure 2:
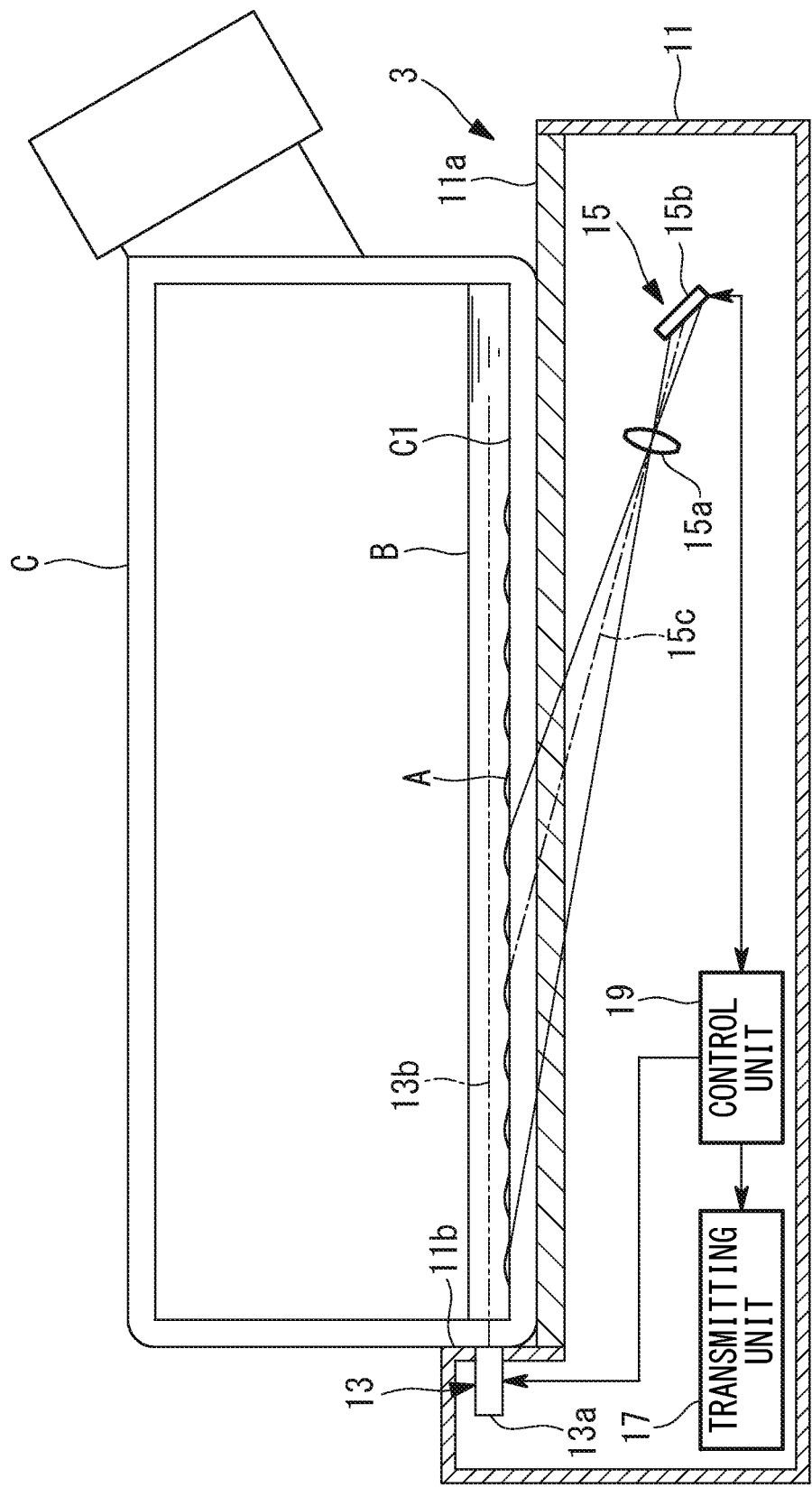
FIG. 2 is a longitudinal sectional view illustrating the culture observation apparatus in FIG. 1.

As illustrated in FIG. 2, the culture observation apparatus 3 includes a base 11 on which is mounted a culture container C containing cells A to be cultured together with a culture solution B, and includes a light source unit 13, an imaging unit 15, a transmitting unit 17, and a control unit 19, which are provided in the base 11.

The culture container C is, for example, a flask for cell culturing and is formed of an optically transparent material. The reference sign C1 indicates a bottom surface of the culture container C.

As illustrated in FIG. 2, the base 11 is provided with a mounting surface 11a composed of an optically transparent material that comes into close contact with a lower surface of the culture container C and an abutment surface 11b provided upright from the mounting surface 11a and brought into close contact with one side surface of the culture container C mounted on the mounting surface 11a. Since the interior of the incubator 9 becomes humid, the base 11 has a waterproof structure.

The light source unit 13 includes a plurality of LED light sources 13a disposed on the abutment surface 11b at a predetermined distance from the mounting surface 11a and arranged in a direction parallel to the mounting surface 11a. An optical axis 13b of illumination light radiated from each of the LED light sources 13a is set to be substantially parallel to the mounting surface 11a.

The imaging unit 15 includes a light-collecting lens 15a disposed below the mounting surface 11a inside the base 11 and an image sensor 15b that acquires images by capturing light collected by the light-collecting lens 15a. The image sensor 15b is disposed on the opposite side to the mounting surface 11a with the light-collecting lens 15a interposed therebetween and is disposed on an optical axis 15c of the light-collecting lens 15a.

The transmitting unit 17 is configured to transmit the images acquired by the image sensor 15b to the outside wirelessly.

The control unit 19, for example, includes a timer (not illustrated) and is configured to periodically operate the light source unit 13, the imaging unit 15, and the transmitting unit 17.

Figure 3:
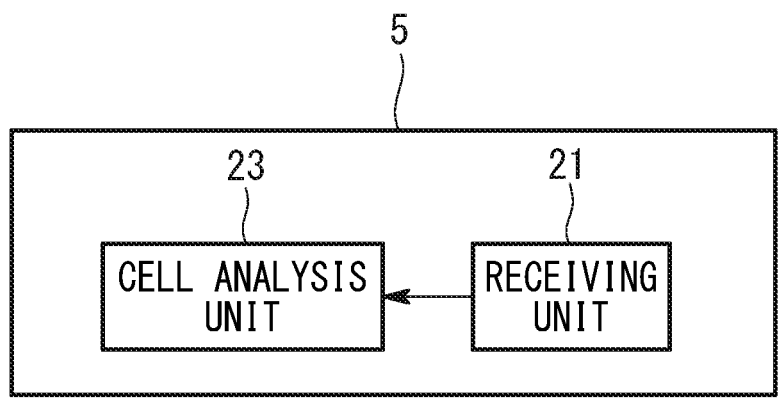
FIG. 3 is a block diagram of a PC main body in FIG. 1.

As illustrated in FIG. 3, the PC main body 5 is provided with a receiving unit 21 that receives the images transmitted from the transmitting unit 17, and a cell analysis unit (image analysis unit, statistical analysis unit) 23 that, on the basis of the images received by the receiving unit 21, quantitatively analyzes the culture state of the cells A being cultured inside the culture container C and statistically analyzes the obtained data.

The cell analysis unit 23 is configured to count the number of cells A being cultured inside the culture container C in accordance with a conventional technique. In addition, the cell analysis unit 23 plots the counted number of cells with respect to a time axis and creates a proliferation curve representing a temporal change in the number of cells A inside the culture container C within each subculture period. The period from after a subculture operation has been performed to the next subculture operation is defined as one subculture period. The proliferation curve of the number of cells for each subculture period generated by the cell analysis unit 23 is sent to the monitor 7 as information related to the number of cells A.

The monitor 7 is configured to display, in a manner allowing comparison thereof, temporal changes in the number of cells inside the culture container C within a plurality of subculture periods on the basis of the information on the numbers of cells A sent from the cell analysis unit 23 (statistical analysis result).

Figure 4:
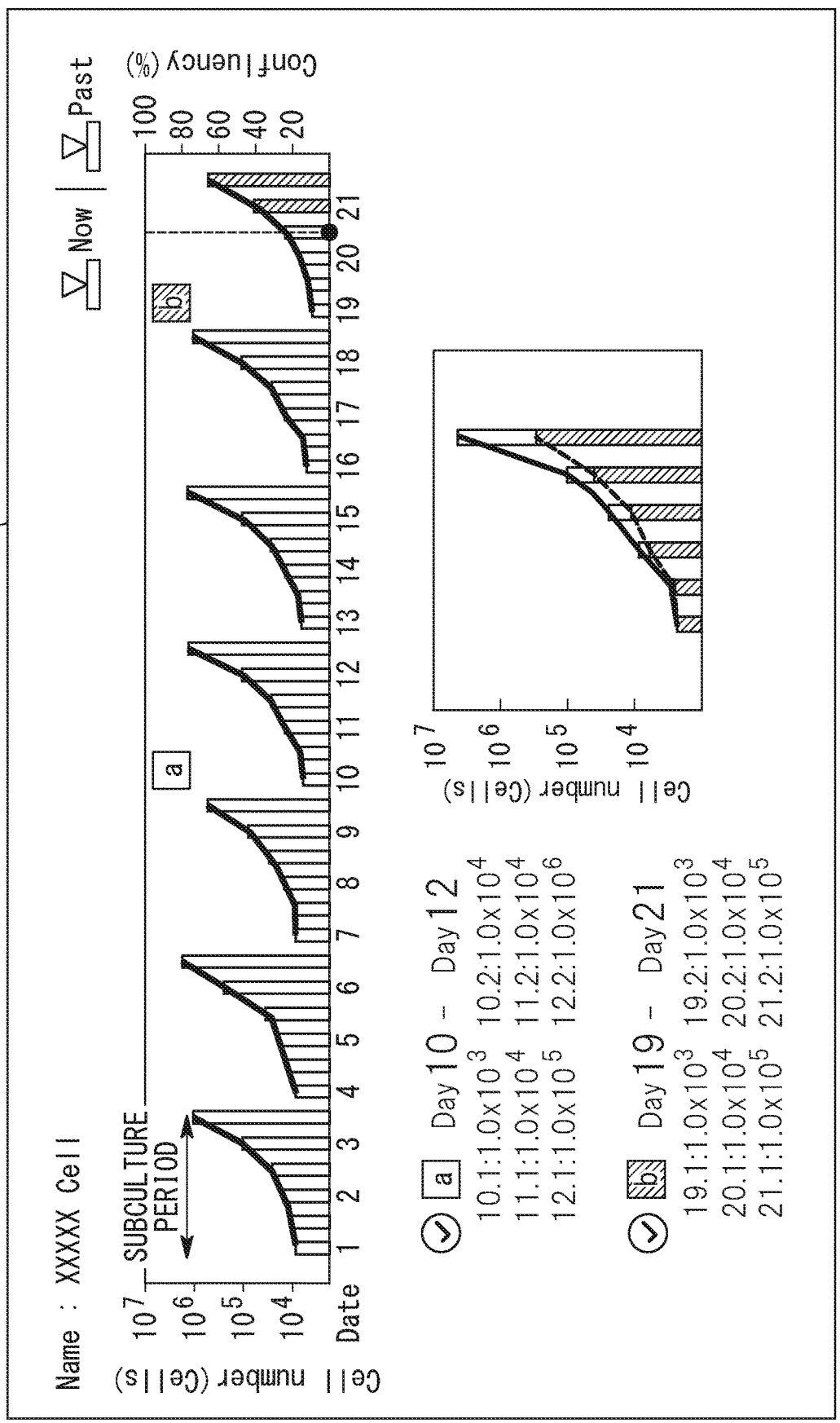
FIG. 4 illustrates an example of a proliferation curve for subculture periods displayed in chronological order on a monitor.

For example, as illustrated in FIG. 4, the monitor 7 is configured to display the proliferation curves of the number of cells for the subculture periods sent from the cell analysis unit 23 in chronological order. In the example illustrated in FIG. 4, with one subculture period being three days, proliferation curves for subculture periods obtained by repeating subcultures from day 1 to day 21 are arranged in series along a time axis.

In addition, the monitor 7 is configured to be capable of superimposing and displaying the proliferation curves for a plurality of subculture periods designated by an operator (user) from among the proliferation curves of the respective subculture periods displayed in chronological order. In the example illustrated in FIG. 4, the proliferation curve for the subculture period a from the 10th day to the 12th day and the proliferation curve for the subculture period b from the 19th day to the 21st day are superimposed and displayed.

The operation of the cell observation system 1 according to the present embodiment thus configured will be described below.

In order to observe the culture state of the cells A using the cell observation system 1 according to the present embodiment, the culture container C containing the cells A to be cultured and the culture solution B is placed on the mounting surface 11a of the base 11 and is mounted on the base 11 such that one side surface thereof abuts against the abutment surface 11b of the base 11.

In this state, the culture observation apparatus 3 with the culture container C mounted thereon is housed in the incubator 9 and is disposed so that the mounting surface 11a is horizontal. As a result, culturing of the cells A inside the culture container C is started in an environment in which the temperature and the humidity inside the incubator 9 are controlled. In addition, at this point in time, the timer inside the control unit 19 is operated to start timekeeping.

When the culturing is started, in accordance with the time measurement result of the timer and a schedule set in advance, the control unit 19 activates the light source unit 13, turns on the LED light sources 13*a*, and causes the image sensor 15*b* to perform imaging.

The LED light sources 13*a* are provided on the abutment surface 11*b* against which the side surface of the culture container C is abutted, and illumination light is made incident on the inside of the culture container C from the side surface of the culture container C in the direction of the optical axis 13*b* along the bottom surface C1 of the culture container C. As a result, in the same way as oblique illumination or dark-field illumination, the cells A adhering to and growing on the bottom surface C1 of the culture container C are illuminated from the side and shadows of the cells A are formed. {0023} A portion of the scattered light scattered by the cells A passes through the bottom surface C1 of the culture container C and the mounting surface 11*a* of the base 11 and is collected by the light-collecting lens 15*a* inside the base 11 and captured by the image sensor 15*b*. In the imaging unit 15, for example, light from the cells A is captured every several hours by the image sensor 15*b*, and an image is acquired.

The LED light sources 13*a* are extinguished each time an image has been acquired. By intermittently operating the light source unit 13 and the like in this way, it is possible to suppress a temperature rise of the apparatus and to reduce the effect of heat on the cells A.

Then, the images obtained over time by the image sensor 15*b* are sent from the control unit 19 to the transmitting unit 17 and are sequentially transmitted to the outside by the transmitting unit 17. On the outside of the incubator 9, the images transmitted from the transmitting unit 17 are sequentially received by the receiving unit 21 of the PC main body 5 and displayed on the monitor 7. As a result, outside the incubator 9, it is possible to confirm the culture state of the cells A inside the culture container C without having to take the culture container C out from the inside of the incubator 9 and perform observation and, furthermore, without having to open the door of the incubator 9. That is, there is an advantage that it is possible to greatly reduce bothersome checking work during cell culturing. In addition, since it is not necessary to take the culture container C out of the incubator 9, it is possible to eliminate environmental changes (changes in temperature, pH, and the like) to the cells A.

The images received by the receiving unit 21 are sequentially sent to the cell analysis unit 23, and the cell analysis unit 23 sequentially counts the number of cells A cultured inside the culture container C on the basis of each image. Then, the cell analysis unit 23 plots the counted number of cells with respect to a time axis to create a proliferation curve of the number of cells inside the culture container C within one subculture period. The cell-number proliferation curve generated by the cell analysis unit 23 is displayed on the monitor 7.

When the proliferated cells A reach a state in which the cells A overspread to a side of the culture container C (confluent), the operator temporarily takes out the culture observation apparatus 3 from the incubator 9 and performs a subculture operation in which a number of cells are diluted and placed in a new culture container C.

Then, after the subculture operation, the new culture container C is mounted on the base 11, and the culture observation apparatus 3 is housed in the incubator 9 again.

Then, similarly to the cells A inside the previous culture container C, the cells A are cultured under an environment in which the temperature and the humidity in the incubator 9 are controlled, and the images thereof are acquired and displayed on the monitor 7. In addition, the cell number is counted by analysis of the images by the cell analysis unit 23, and a proliferation curve of the number of cells inside the culture container C within a subculture period is created and displayed on the monitor 7. This is repeated for multiple subculture periods.

On the monitor 7, as illustrated in FIG. 4, proliferation curves of the number of cells inside the culture container C within a plurality of subculture periods are displayed in series along a time axis. By performing display in such a manner, it is easy to compare the temporal changes in the number of cells inside the culture container C for the subculture periods. In addition, when the cells A deteriorate and the proliferative capacity decreases with the repetition of subcultures, because the upward curve of the proliferation curve becomes more gentle, depending on the slope of the proliferation curve for each subculture period, it is possible to grasp the change in the proliferative capacity of the cells A for the subculture periods at a glance.

In addition, when the operator designates any of the plurality of proliferation curves for the subculture periods, the designated proliferation curves for the subculture periods are superimposed and displayed on the monitor 7. As a result, it is possible to grasp the difference in the proliferative capacity of the cells A for a plurality of subculture periods of interest at a glance.

Figure 5:
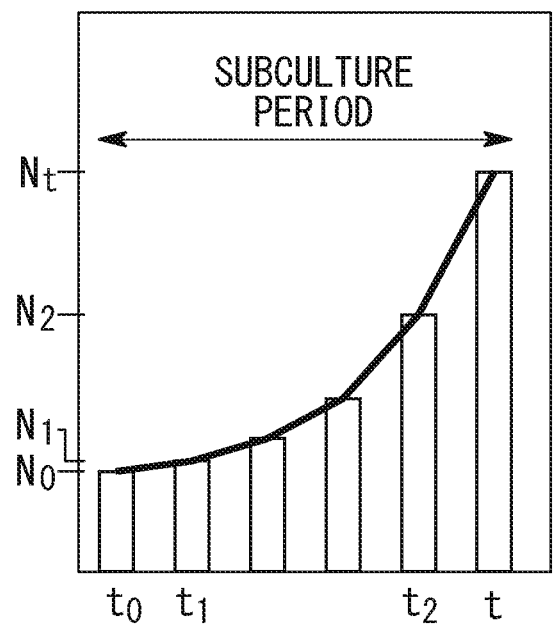
FIG. 5 is a diagram illustrating an example of a proliferation curve of the number of cells within one subculture period.

In addition, the operator can evaluate the degree of degradation of the cells A by using the change in the proliferation curves for the subculture periods as an index. For example, the slopes of the proliferation curves for the subculture periods may be calculated and quantitatively compared using the calculated slope of each proliferation curve as an index. In this case, for example, as illustrated in FIG. 5, when the number of cells at the beginning of the subculture period (time $t_0$) is $N_0$, assuming that the number of cells at the end of the subculture period (time t) is $N_t$, the slope a of the proliferation curve can be calculated as $a=(N_t-N_0)/(t-t_0)$.

In addition, it is also possible to calculate the slope of two arbitrary points of the subculture period and compare them quantitatively using the calculated slope of the two points as an index. Assuming that the number of cells at an arbitrary time point (time $t_1$) is $N_1$ and the number of cells at another time point (time $t_2$) is $N_2$, the slope a of the proliferation curve can be calculated as $a=(N_2-N_1)/(t_2-t_1)$.

Alternatively, the proliferation rate may be calculated and quantitatively compared using a calculated proliferation rate as an index. In this case, the proliferation rate a can be calculated as $(N_t-N_0)/N_0$. When the number of cells at an arbitrary time point (time $t_1$) is set as $N_1$ and the number of cells at another time point (time $t_2$) is set as $N_2$, the proliferation rate a can be calculated as $(N_2-N_1)/N_1$.

In addition, for the proliferation curves of respective subculture periods, the times (doubling times) required to double the cell number may be calculated and quantitatively compared using the calculated doubling times as an index. In this case, the doubling time T can be calculated as $(t-t_0)\log_{10} 2/\log_{10}(N_t/N_0)$ or $(t-t_0)/\log_2(N_t/N_0)$.

In addition, the doubling time of two arbitrary points of the subculture period may be calculated and quantitatively compared using the calculated doubling time as an index. Assuming that the number of cells at an arbitrary time point (time $t_1$) is $N_1$ and the number of cells at another time point (time $t_2$) is $N_2$, the doubling time T can be calculated as $(t_2-t_1) \log_{10} 2/\log_{10}(N_2/N_1)$ or $(t_2-t_1)/\log_2 (N_2/N_1)$. Here, t1 and t2 are preferably two arbitrary points in the logarithmic proliferation phase.

As described above, according to the cell observation system 1 according to the present embodiment, by displaying, in a manner allowing comparison thereof, the temporal changes in the number of cells in the culture container C within a plurality of subculture periods by using the monitor 7, it is possible to visually recognize the change in the proliferative capacity of the cells A during the subculture periods without requiring a complex algorithm. As a result, it is possible to evaluate the quality of cells with a simple operation without much effort.

In addition, since the imaging unit 15 captures the scattered light transmitted through the bottom surface C1 of the culture container C among the scattered light in the cells A that are being cultured, when the cells A are cultured under a high-temperature and high-humidity environment, it is possible to acquire a clear image without being affected by water droplets formed by condensation on the upper surface of the culture container C.

In addition, in the present embodiment, since the LED light sources 13a are used as the light source unit 13, there is an advantage that heat generation can be suppressed, the impact on the cells A can be reduced, and power consumption can be suppressed.

In the present embodiment, the cell density (cell number per unit area) may be calculated instead of the cell number, and the calculated cell density may be plotted against a time axis to create a cell proliferation curve. In addition, the area occupied by the cells A in the culture container C may be calculated instead of the cell number, and the calculated area may be plotted with respect to a time axis to create a cell proliferation curve.

In addition, in the present embodiment, for example, the cell analysis unit 23 may function as a comparing unit that compares the temporal changes in the number of cells for the subculture periods and outputs a change in the proliferation rate of the cells A. By doing so, the operator can easily grasp a change in the proliferative capacity of the cells A for each subculture period, and it is possible to save the operator the trouble of comparison.

In addition, in the present embodiment, for example, the cell analysis unit 23 may function as a quality evaluation unit that evaluates the quality of the cells A on the basis of the proliferation rate of the cells A in each subculture period. By doing so, the cell analysis unit 23 can easily evaluate the cells A having a desired quality.

In this case, for example, when the proliferation rate of the cells A is higher than a predetermined threshold at the end of the culture process, it may be determined that the quality of the cells A in the culture container C is good. In addition, because the cell-number doubling time becomes long when the cells A degrade and the proliferative capacity decreases, in the case where the doubling time until a predetermined cell number has been reached is shorter than a predetermined threshold value, it may be determined that the quality of the cells A in the culture container C is good.

In addition, in the present embodiment, the illumination light from the light source unit 13 is made incident on the inside of the culture container C in the horizontal direction along the optical axis 13b parallel to the bottom surface C1 of the culture container C; however, the illumination light from the light source unit 13 may be made incident on the culture container C at an angle of ±30° or less with respect to the horizontal direction. Even if such an angle is adopted, a shadow similar to that in dark-field illumination or oblique illumination can be formed on the cells A, and a stereoscopic image can be captured.

Figure 6:
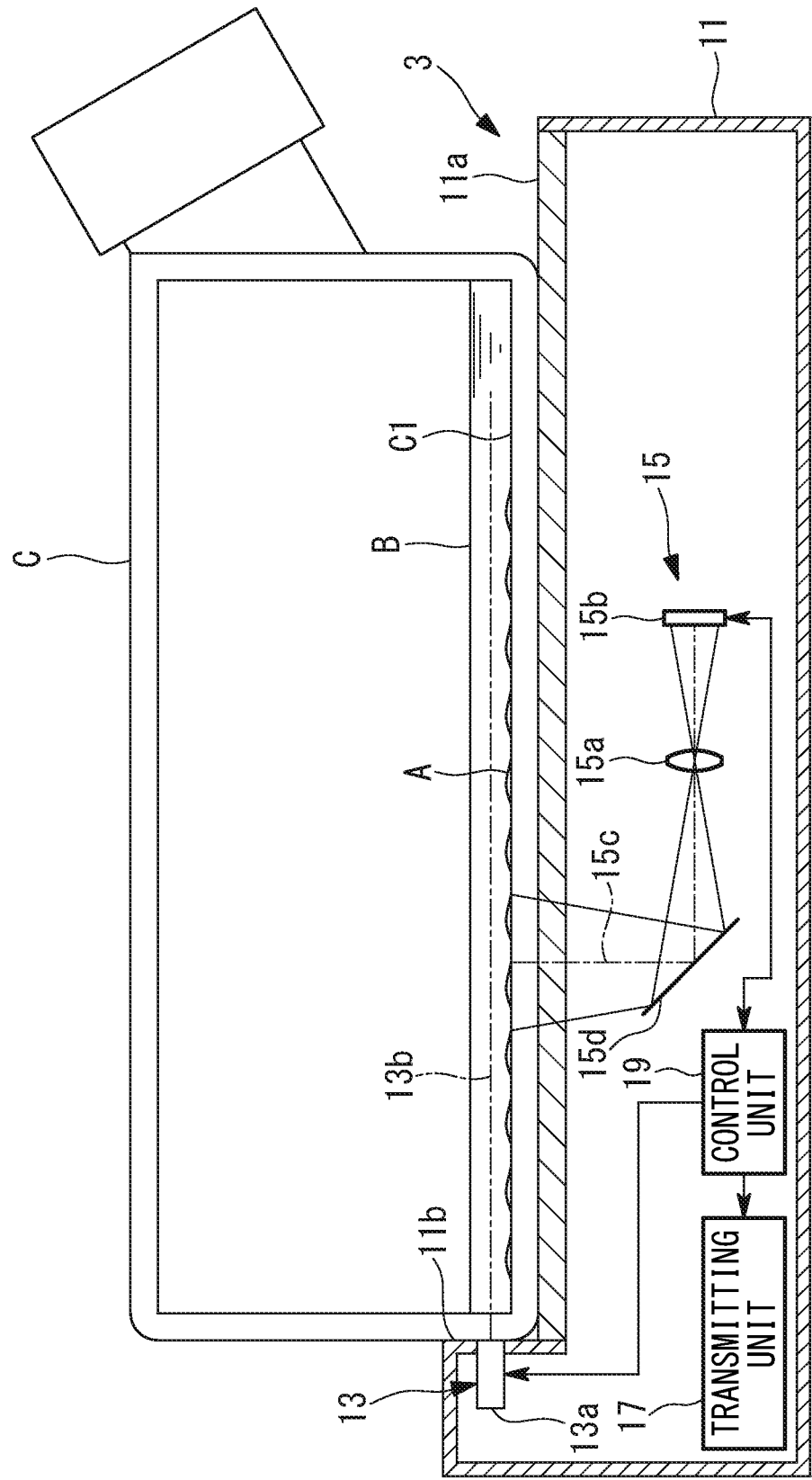
FIG. 6 is a longitudinal sectional view illustrating a modification of the culture observation apparatus in FIG. 2.

In addition, in the present embodiment, as illustrated in FIG. 6, a partial image of the bottom surface C1 may be acquired by making the optical axis 15c of the light-collecting lens 15a perpendicular to the bottom surface C1 of the culture container C. In this case, for example, the optical axis 15c of the light-collecting lens 15a may be bent by one or more mirrors 15d. Even though the reliability of determination of the culture state is reduced as compared with the case of capturing an image of the entire bottom surface C1 of the culture container C or a relatively wide portion of the bottom surface C1, the culture state may be estimated from the image of the partial region.

In addition, in the present embodiment, the control unit 19 is provided with a timer to periodically operate the light source unit 13 and the like, but in place of this, a receiving unit (not illustrated) may be connected to the control unit 19 and may receive a command signal from outside of the incubator 9, and the control unit 19 may drive the light source unit 13 and the like in accordance with the command signal. The light source unit 13 may be turned on and off or image capturing may be performed by remote control in accordance with an instruction previously input by the operator, or the operator may turn on and off the light source unit 13 or perform image capturing by remote control at an arbitrary timing.

The transmission and reception of image signals and command signals may be performed wirelessly or via wires.

In the present embodiment, a mode of displaying the cell proliferation curve is illustrated, but the curve may be displayed as a straight line by plotting on a logarithmic axis. By doing so, the portion corresponding to the logarithmic proliferation phase in the subculture period is displayed as a straight line, and it is possible to grasp and compare cell proliferation capacities more intuitively.

In addition, instead of the cell proliferation curve, the change in the number of cells may be displayed as a bar graph or as discontinuous dots (points).

Second Embodiment

Next, a cell observation system according to a second embodiment of the present invention will be described below with reference to the drawings.

Figure 7:
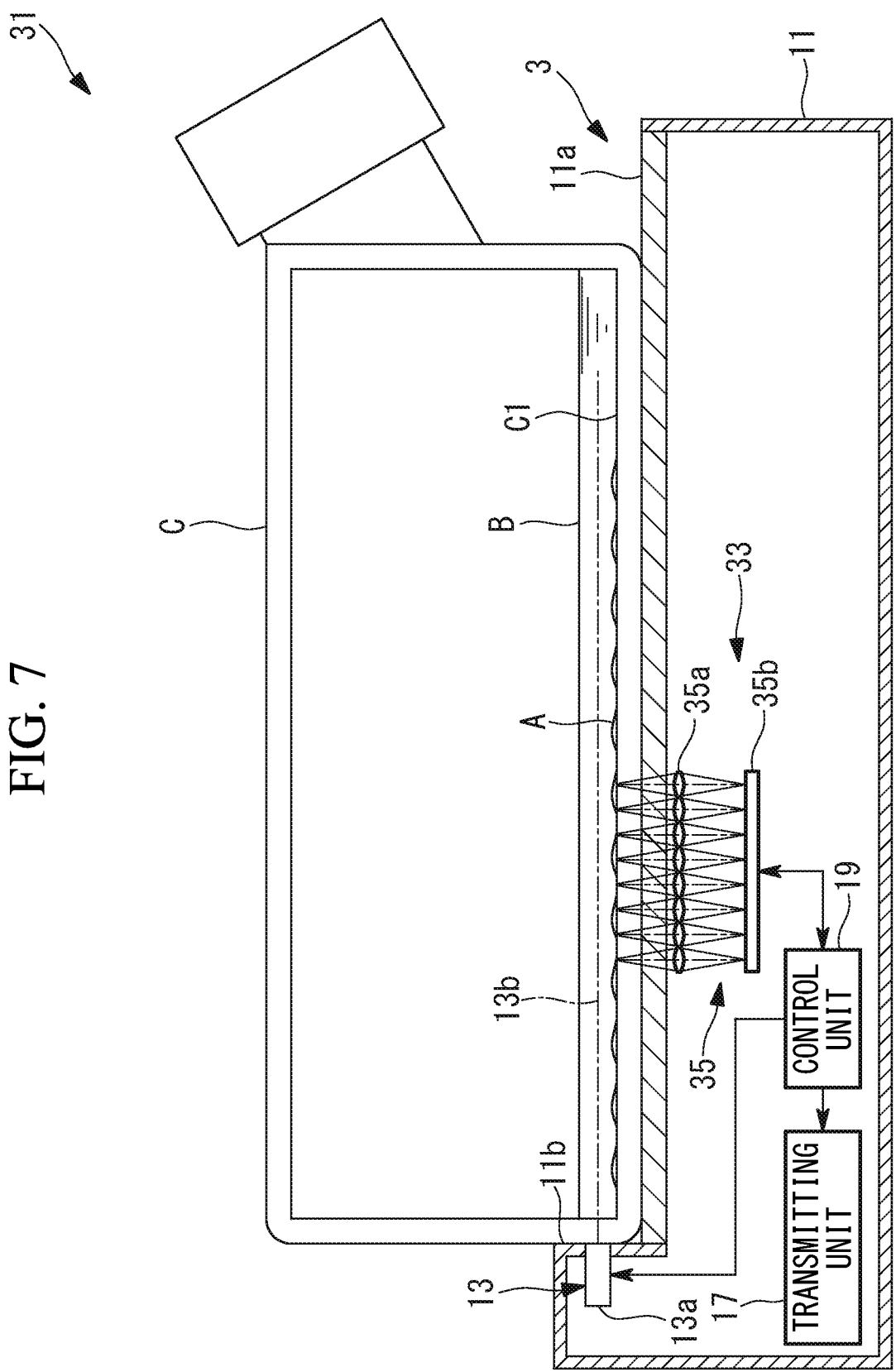
FIG. 7 is a longitudinal sectional view illustrating a culture observation apparatus of a cell observation system according to a second embodiment of the present invention.

As illustrated in FIG. 7, a cell observation system 31 according to the present embodiment differs from the cell observation system 1 according to the first embodiment in terms of an imaging unit 33.

In the description of the present embodiment, the same reference numerals are given to elements having the same configuration as those in the cell observation system 1 according to the above-described first embodiment, and a description thereof will be omitted.

The imaging unit 33 includes a microlens array 35 having a plurality of microlenses 35a disposed in a plane substantially parallel to the mounting surface 11a below the mounting surface 11a of the base 11 and an imaging element 35b disposed further below the microlens array 35. Each of the microlenses 35a of the microlens array 35 is disposed so as to correspond to a respective pixel of the imaging element 35b.

The focal length of each of the microlenses 35a is set to be larger than the thickness dimension obtained by adding the thickness dimension of the transparent member constituting the mounting surface 11a and the thickness dimension of the bottom surface C1 of the culture container C mounted on the mounting surface 11a. Each of the microlenses 35a is configured such that it is disposed under the mounting surface 11a with its focal position aligned with the cells A adhering to the bottom surface C1 of the culture container C so that an image of the cells A is projected onto the imaging surface of the imaging element 35b.

It is not always necessary for the imaging element 35b to capture an image of the entire bottom surface C1 of the culture container C, and an image may be acquired for an arbitrary partial region such as a center portion in which the cells A are likely to be present, and the culture state may be estimated on the basis of the acquired image.

Third Embodiment

Next, a cell observation system according to a third embodiment of the present invention will be described below with reference to the drawings.

Figure 8:
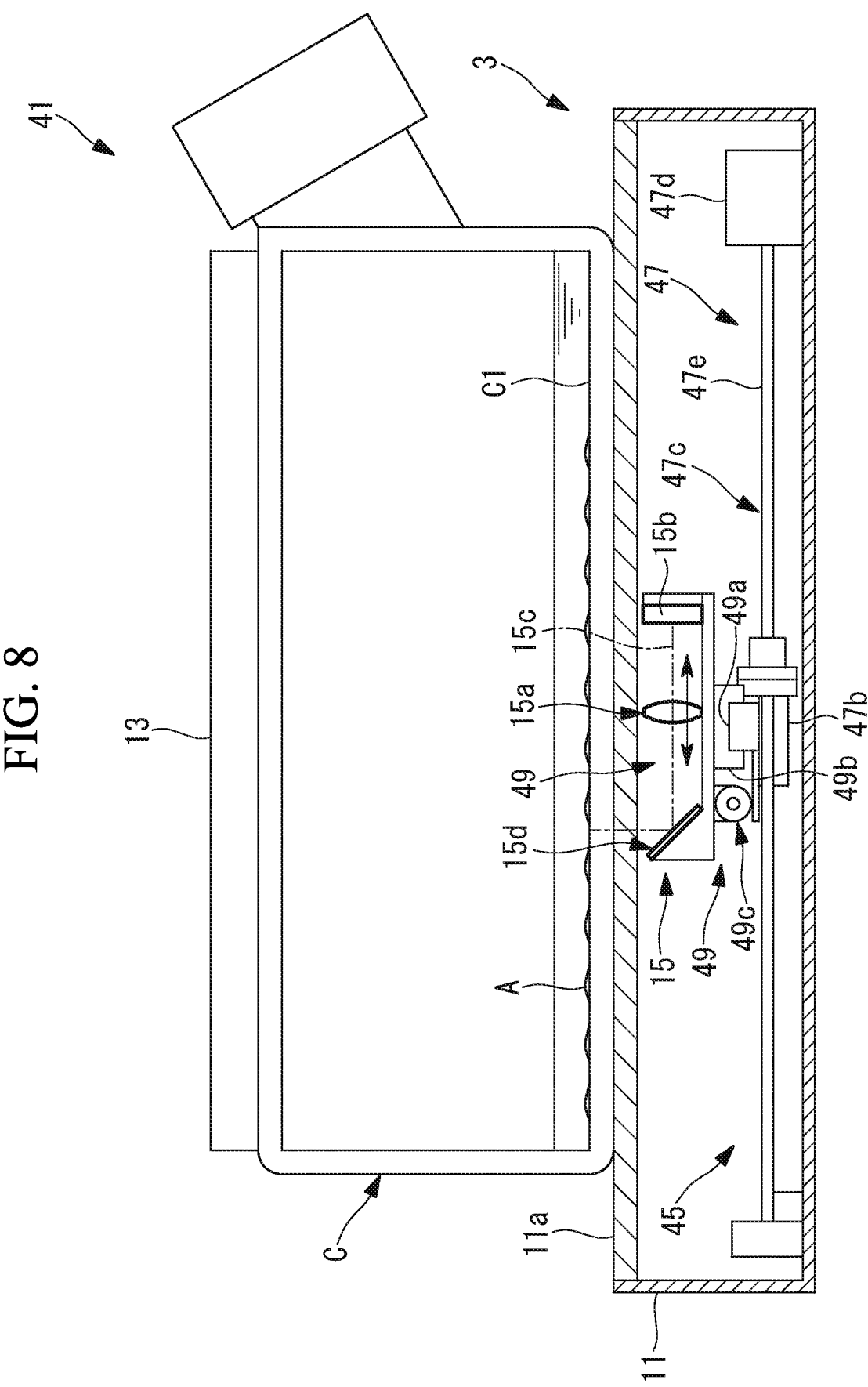
FIG. 8 is a longitudinal sectional view illustrating a culture observation apparatus of a cell observation system according to a third embodiment of the present invention.
Figure 9:
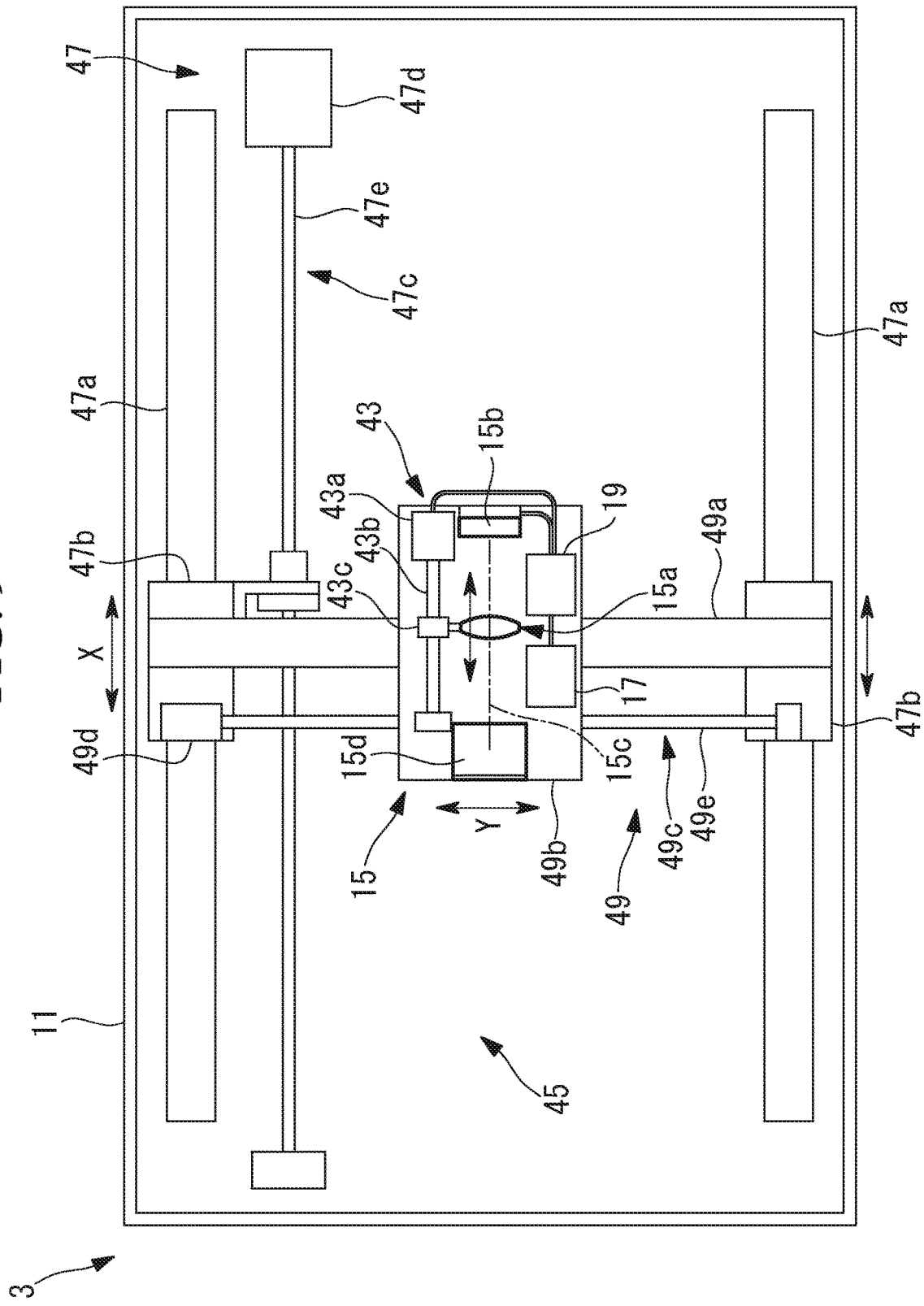
FIG. 9 is a plan view illustrating the internal structure of the culture observation apparatus in FIG. 8.

As illustrated in FIGS. 8 and 9, a cell observation system 41 according to the present embodiment includes a focus adjustment mechanism 43 that moves the light-collecting lens 15a of the imaging unit 15 in a direction along the optical axis 15c, and a movement mechanism 45 that two-dimensionally moves the imaging unit 15 in a direction along the mounting surface 11a.

In the description of the present embodiment, the same reference numerals are given to elements having the same configuration as those in the cell observation system 1 according to the above-described first embodiment, and a description thereof will be omitted.

The focus adjustment mechanism 43 is, for example, a linear movement mechanism including a motor 43a and a ball screw 43b. The focus adjustment mechanism 43 is configured to rotate the ball screw 43b by operation of the motor 43a and linearly move a nut 43c, which meshes with the ball screw 43b, along the optical axis 15c of the light-collecting lens 15a so that the light-collecting lens 15a fixed to the nut 43c can be moved along the optical axis 15c thereof.

As illustrated in FIG. 9, the movement mechanism 45 is formed of two linear movement mechanisms 47 and 49 disposed perpendicular to each other. The first linear movement mechanism 47 includes a guide rail 47a fixed to the base 11, a slider 47b supported so as to be movable in a first horizontal direction X along the guide rail 47a, and a driving mechanism 47c that moves the slider 47b. The driving mechanism 47c includes a motor 47d and a ball screw 47e.

In addition, the second linear movement mechanism 49 includes a guide rail 49a fixed to the slider 47b of the first linear movement mechanism 47, a slider 49b supported so as to be movable in a second horizontal direction Y along the guide rail 49a, and a driving mechanism 49c that moves the slider 49b. The driving mechanism 49c includes a motor 49d and a ball screw 49e.

The operator confirms whether or not the focal point of the light-collecting lens 15a appropriately matches the cells A by using the image acquired by the image sensor 15b, and, when they do not match each other, inputs a command signal for operating the focus adjustment mechanism 43 in either direction and operates the focus adjustment mechanism 43 by using the control unit 19.

When the ball screw 43b is rotated by the rotation of the motor 43a, the nut 43c moves in one of the horizontal directions in accordance with the rotation direction of the ball screw 43b and, as a result of the light-collecting lens 15a fixed to the nut 43c being moved in the horizontal direction, the focus position of the light-collecting lens 15a is moved in the up/down direction.

That is, when the light-collecting lens 15a is moved in a direction toward the mirror 15d, the focal position is raised, and when the light-collecting lens 15a is moved in a direction away from the mirror 15d, the focal position is lowered. In this way, it is possible to obtain a clear image by adjusting the focal position to an appropriate position.

In addition, when wanting to observe different positions, the operator inputs a command signal for moving the movement mechanism 45 in one of the directions and operates the movement mechanism 45 by using the control unit 19. The observation position is moved in the horizontal direction Y by moving the imaging unit 15 along the second linear movement mechanism 49, and the observation position is moved in the horizontal direction X by moving the second linear movement mechanism 49 and the imaging unit 15 along the first linear movement mechanism 47. In this way, the observation position can be two-dimensionally adjusted.

The light source unit 13 of the present embodiment may be disposed at a position so as to illuminate the culture container C from above. In addition, the light source unit 13 may be arranged at a position so as to illuminate the culture container C from a side surface thereof. In addition, the light source unit 13 may be disposed at a position so as to illuminate the culture container C from the bottom surface thereof or the light source unit 13 may be moved by the movement mechanism 45 together with the imaging unit 15.

Fourth Embodiment

In the first embodiment and the second embodiment, a mode in which illumination light is radiated to the cells A from the side is illustrated; however, a mode in which illumination light is radiated to the cells A from below will be described below.

Figure 10:
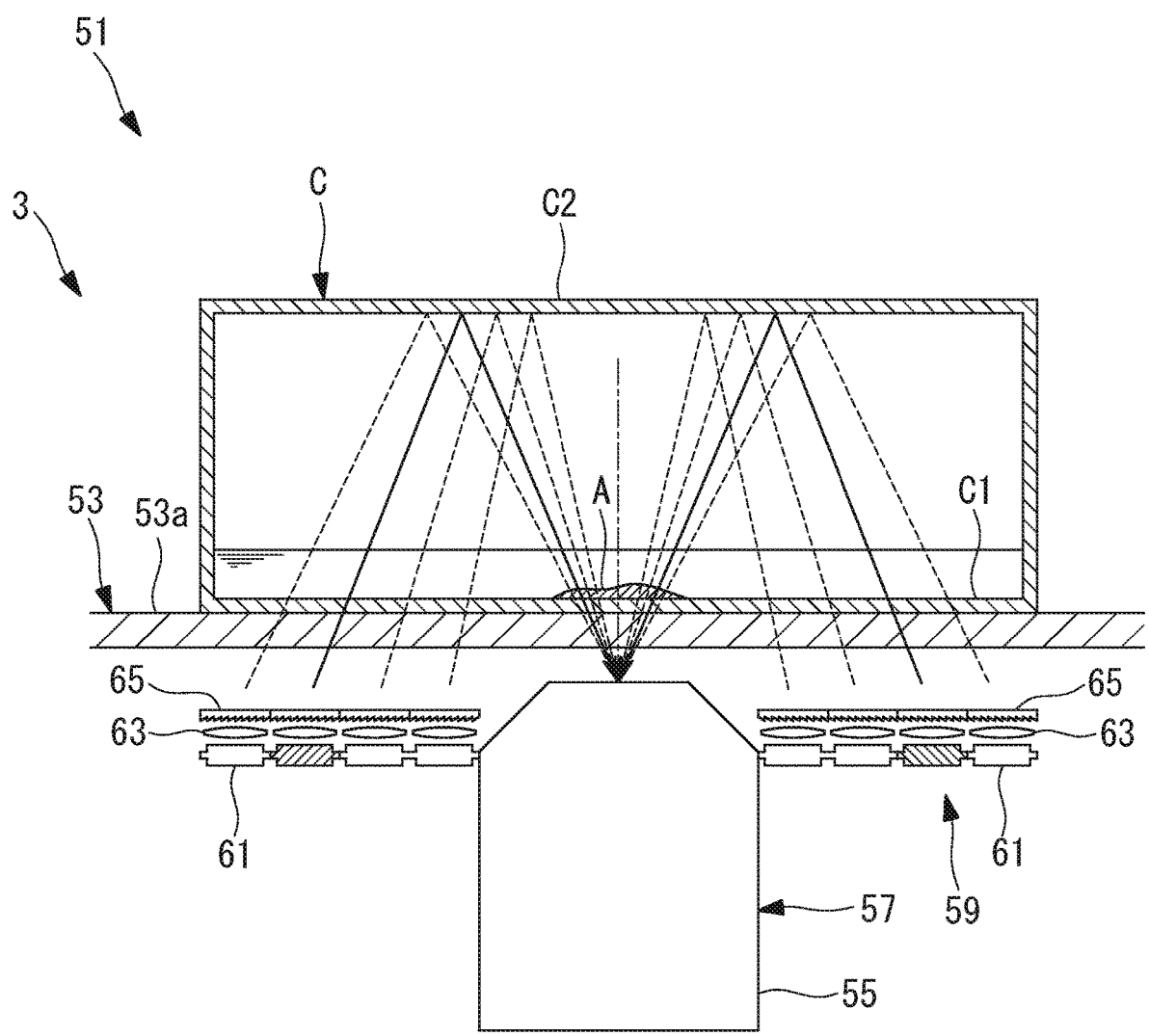
FIG. 10 is a partial longitudinal sectional view illustrating a culture observation apparatus of a cell observation system according to a fourth embodiment of the present invention.

As illustrated in FIG. 10, in a cell observation system 51 according to the present embodiment, the culture observation apparatus 3 includes a stage 53 on which the culture container C containing the cells A is placed, an objective lens 55 that is disposed below the stage 53 and that collects the light transmitted from above the stage 53, an imaging optical system 57 for capturing light transmitted through the cells A, and a light source unit 59 that is disposed radially outward of the objective lens 55 and that radiates illumination light upward through the stage 53.

In order to cover the upper side of the objective lens 55 and the light source unit 59, an optically transparent material, for example, a glass plate 53a, is disposed on the stage 53, and the culture container C is placed on an upper surface of the glass plate 53a.

The bottom surface of the culture container C is indicated by C1, and a top plate of the culture container C is indicated by C2.

Figure 11:
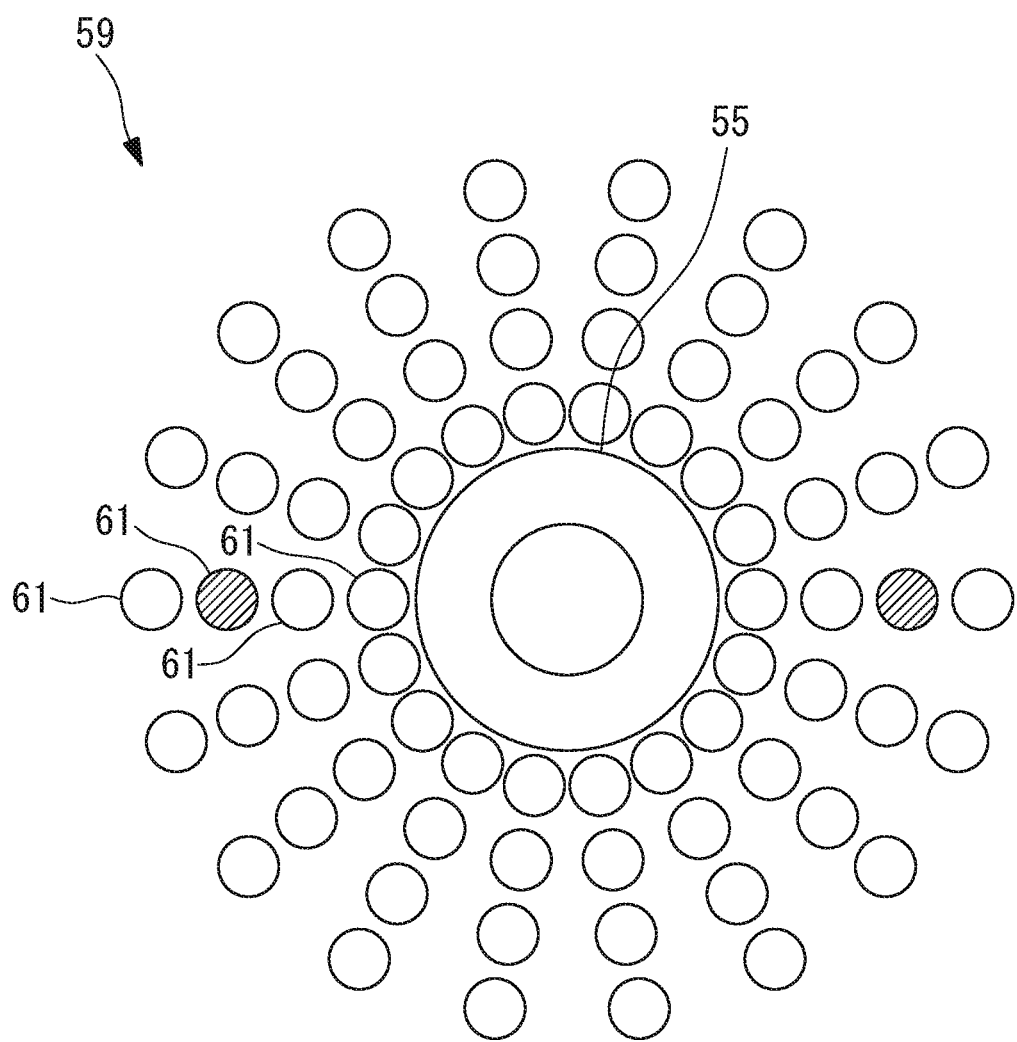
FIG. 11 is a plan view illustrating an example of an arrangement of LED light sources in a light source unit of the culture observation apparatus in FIG. 10.
Figure 12:
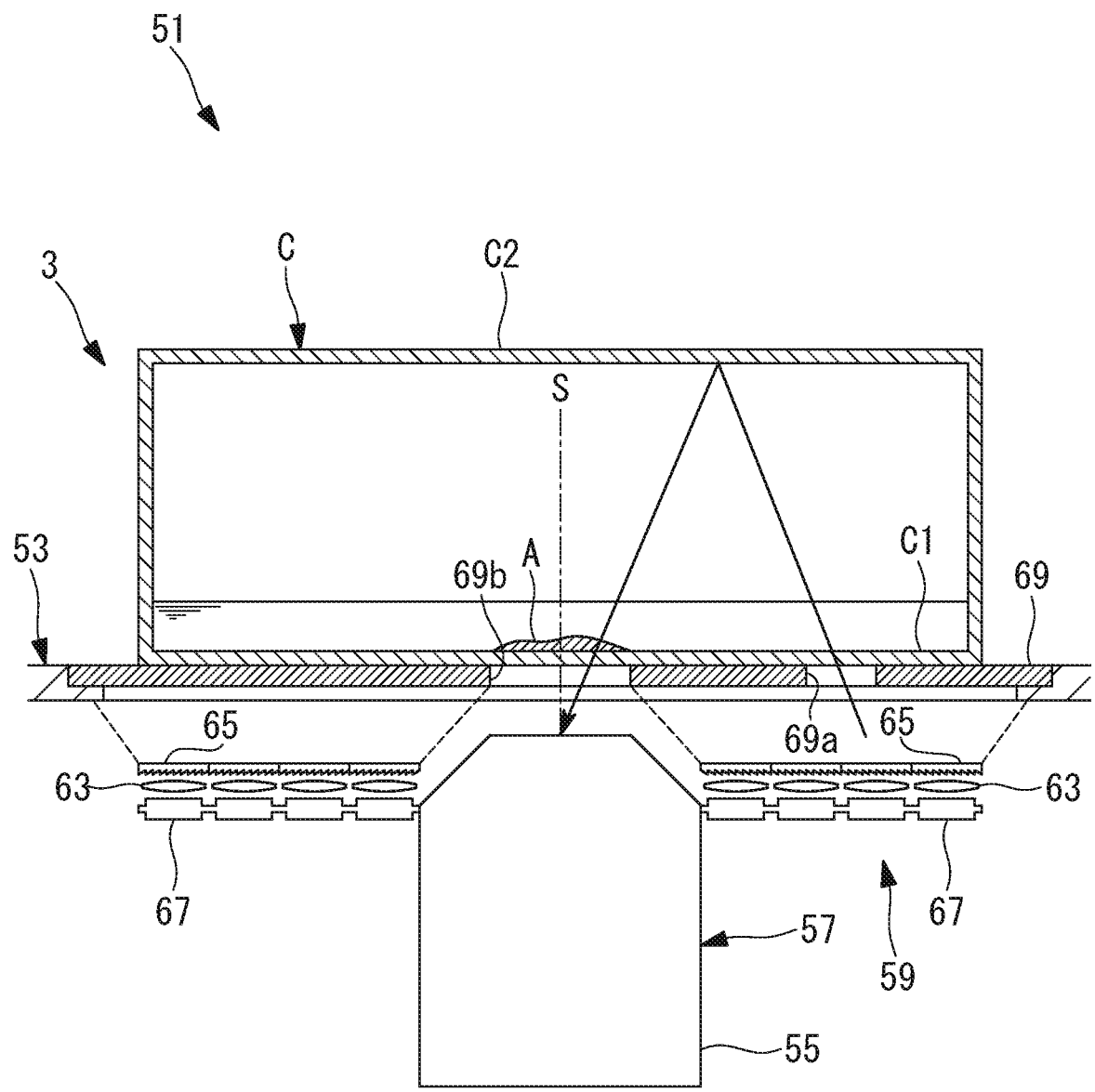
FIG. 12 is a partial longitudinal sectional view illustrating a case where illumination light is limited by using a light blocking member, the light blocking member being a modification of the culture observation apparatus in FIG. 10.

As illustrated in FIGS. 10 and 11, the light source unit 59 includes, around the objective lens 55, a plurality of LED light sources (light source) 61 disposed so as to be spaced apart in circumferential and radial directions, a plurality of collimating lenses 63 that are disposed so as to correspond to respective light sources of the LED light sources 61 and that convert illumination light generated by each of the LED light sources 61 into substantially parallel light, and a diffusion plate 65 that diffuses the illumination light substantially collimated by the collimating lens 63.

The light source unit 59 is configured to be capable of independently lighting specific light sources of the LED light sources 61 (FIGS. 10 and 11 illustrate the LED light sources 61 that are lit by hatching).

That is, by turning on only specific light sources of the LED light sources 61 at different positions in the radial direction of the objective lens 55 as indicated by the solid lines in FIG. 10, the angle at which the illumination light is incident on the objective lens 55 after having passed through the glass plate 53a and the bottom surface C1 of the culture container C from the bottom to the top, having been reflected on an inner surface of the top plate C2 of the culture container C, and having passed through the cells A, the bottom surface C1 of the culture container C, and the glass plate 53a obliquely from above can be changed as indicated by the broken lines.

In addition, by turning on only specific light sources of the LED light sources 61 at specific positions in the circumferential direction of the objective lens 55, it is possible to illuminate the cells A only from a specific direction in the circumferential direction. In addition, as illustrated in FIG. 11, by turning on the LED light sources 61 disposed in two or more directions in the circumferential direction of the objective lens 55, in particular, axi-symmetric with respect to an optical axis S of the objective lens 55, illumination light with reduced illumination unevenness can be radiated to the cells A.

An observation method using the cell observation system 51 according to the present embodiment thus configured will be described below.

In order to observe the transparent cells A using the cell observation system 51 according to the present embodiment, as illustrated in FIG. 10, in a state where the cells A are adhered to the bottom surface C1 of the culture container C, the culture container C is placed on the glass plate 53a of the stage 53 so that the bottom surface C1 thereof is downward.

In this state, any of the LED light sources 61 of the light source unit 59 are operated to generate illumination light. The illumination light generated by the LED light sources 61 is made into substantially parallel light by the collimating lenses 63 disposed so as to correspond to the LED light sources 61, and in a state of being diffused by the diffusion plate 65, passes through the glass plate 53a and the bottom surface C1 of the culture container C from the bottom upward, and is reflected by the inner surface of the top plate C2 of the culture container C and radiates the cells A obliquely from above.

Among the illumination light radiated on the cells A, the transmitted light of the illumination light transmitted through the cells A passes through the bottom surface C1 of the culture container C and the glass plate 53a from the top downward and is incident on the objective lens 55. At this time, since the illumination light is refracted and scattered depending on the shape and refractive index of the cells A or attenuated depending on the transmittance of the cells A, it becomes transmitted light carrying information about the cells A and is collected by the objective lens 55 and captured by an imaging element, which is not illustrated.

As described above, with the cell observation system 51 according to the present embodiment, because the imaging optical system 57 including the light source unit 59 and the objective lens 55 is disposed below the cells A, compared with a transmitted-light observation device in which a light source unit and an imaging optical system are disposed on either side of the cells A, there is an advantage that the light source unit 59 and the imaging optical system 57 can be collectively disposed on only one side of the cells A and the device can be made thinner. In addition, even in the cell observation system 51 with reduced thickness such as that described above, there is an advantage that an object such as a cell can be observed without labeling by capturing transmitted light.

In addition, because the illumination light from the light source unit 59 is radiated from obliquely above the cells A and is collected by the objective lens 55 by being radiated from radially outside the objective lens 55 and being reflected by the inner surface of the top plate C2 of the culture container C, by appropriately setting the angle of incidence on the cells A, there is an advantage that it is possible to form light and dark areas on the image of the cells A and obtain an image that is easy to see even for a transparent subject such as a cell.

In addition, in the present embodiment, because the light source unit 59 includes a plurality of the LED light sources 61, which are capable of being independently lit, disposed in the radial direction around the objective lens 55 as indicated by broken lines in FIG. 10, by changing the radial-direction positions of the LED light sources 61 to be turned on, the irradiation angle of the illumination light incident on the cells A can be changed. Accordingly, in the case of an incidence angle smaller than the capturing angle of the objective lens 55, in the case of bright field illumination with less illumination unevenness and with an incidence angle larger than the capturing angle of the objective lens 55, and in the case of dark field illumination in which a fine structure is emphasized and the incidence angle is equal to the capturing angle of the objective lens 55, it is possible to achieve oblique illumination in which cells A appear stereoscopically.

In addition, in the present embodiment, because the light source unit 59 includes a plurality of the LED light sources 61 disposed in the circumferential direction around the objective lens 55 and capable of being independently lit, by changing the position in the circumferential direction of the LED light sources 61 to be turned on, the irradiation direction of the illumination light incident on the cells A can be changed. As a result, it is possible to change how the cells A look by changing the direction of shadows in the to-be-formed image of the cells A.

In addition, as illustrated in FIG. 11, by simultaneously turning on a plurality of the LED light sources 61 at different positions in the circumferential direction, particularly, by simultaneously turning on a plurality of the LED light sources 61 arranged axi-symmetrically, there is an advantage that an image of the cells A with less unevenness can be obtained by reducing illumination unevenness.

In addition, in the present embodiment, because the diffusion plate 65 corresponding to each of the LED light sources 61 is provided, the illumination light emitted from the LED light sources 61 is uniformly diffused and illumination light with uniform intensity with less illumination unevenness can be radiated to the cells A.

In the present embodiment, by disposing the plurality of LED light sources 61 in an array and lighting them independently, the irradiation angle and irradiation direction of the illumination light, and the like are changed; however, instead of this, as illustrated in FIGS. 12, 13A, 13B, 13C, 14A, and 14B, the light source unit 59 may include: light sources 67 disposed around the objective lens 55; and a light blocking member 69 that is disposed above the light sources 67 and that blocks illumination light from the light sources 67.

That is, the light blocking member 69 is provided with an opening portion 69a that opens partially in the circumferential direction or the radial direction, and a transmission hole 69b that transmits light that has been reflected by the inner surface of the top plate C2 of the culture container C and transmitted through the cells A, and by shifting the light blocking member 69, the position of the opening portion 69a can be adjusted to change the irradiation angle and irradiation direction of the illumination light.

The light source unit 59 may be provided with the LED light sources 61, which are disposed in an array in the same manner as described above, the collimating lens 63, and the diffusion plate 65; however, the function of changing the light emitting position of the illumination light is not necessary, and a light source unit having arbitrary light sources may be adopted as long as the light sources are capable of emitting illumination light from a wider area than the opening portion 69a.

Figure 13A:
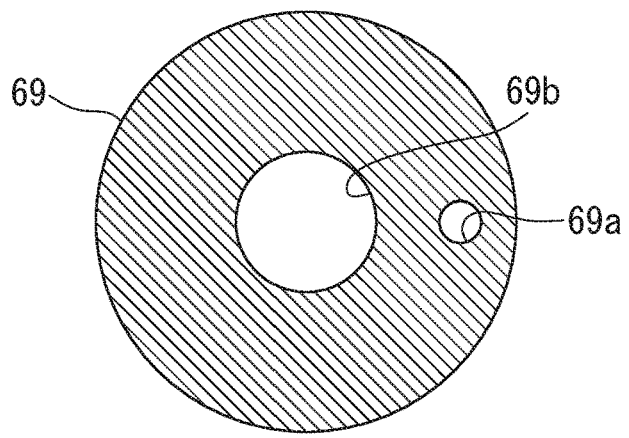
FIG. 13A is a plan view of an example of the light blocking member in FIG. 12 and illustrates a case where a single circular opening portion is provided.
Figure 13B:
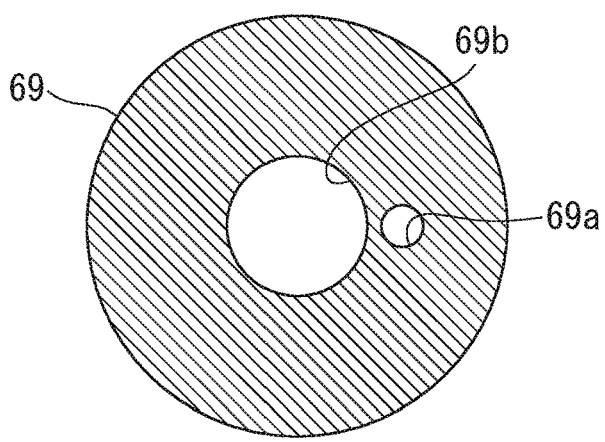
FIG. 13B is a plan view of an example of the light blocking member in FIG. 12 and illustrates a case where the position of the opening portion in the radial direction is different from FIG. 13A.
Figure 13C:
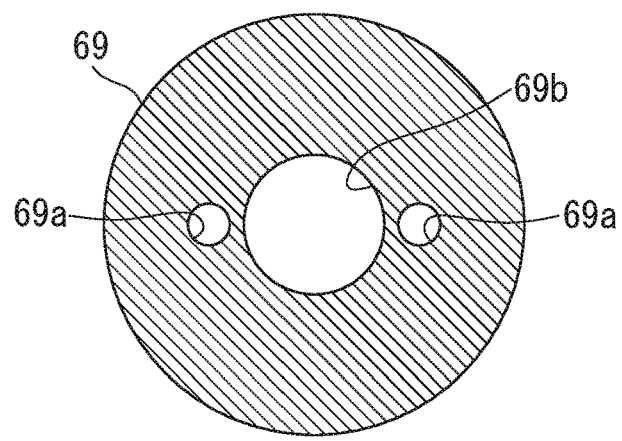
FIG. 13C is a plan view illustrating an example of the light blocking member in FIG. 12 and illustrates a case where two opening portions are provided.
Figure 14A:
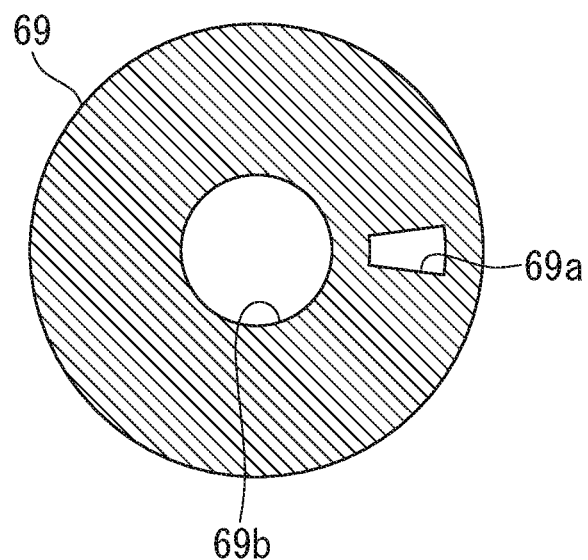
FIG. 14A is a plan view of another example of the light blocking member in FIG. 12 and illustrates a case where a fan-shaped opening is provided.
Figure 14B:
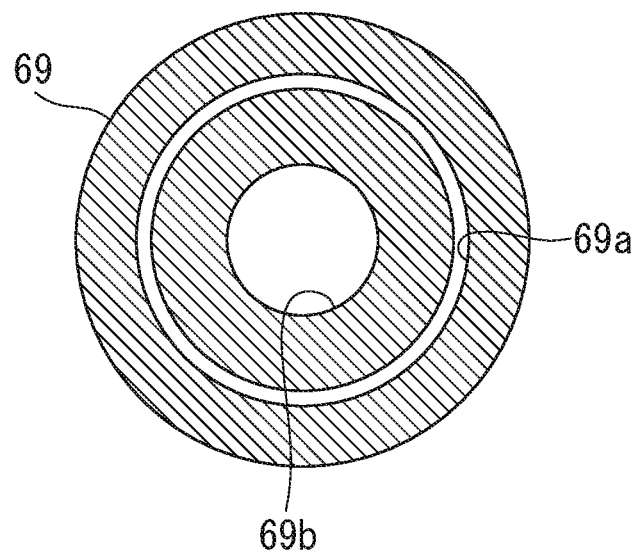
FIG. 14B is a plan view of another example of the light blocking member in FIG. 12 and illustrates a case where an annular-shaped opening portion is provided.

FIGS. 13A to 13C illustrate examples in which the opening portion 69a has a circular shape and in which the radial direction and the number of the opening portions 69a are different. FIG. 14A illustrates a case where the opening portion 69a has a fan shape, and FIG. 14B illustrates a case where the opening portion 69a has an annular shape. An arbitrary size, position and shape of the opening portion 69a can be adopted.

Figure 15:
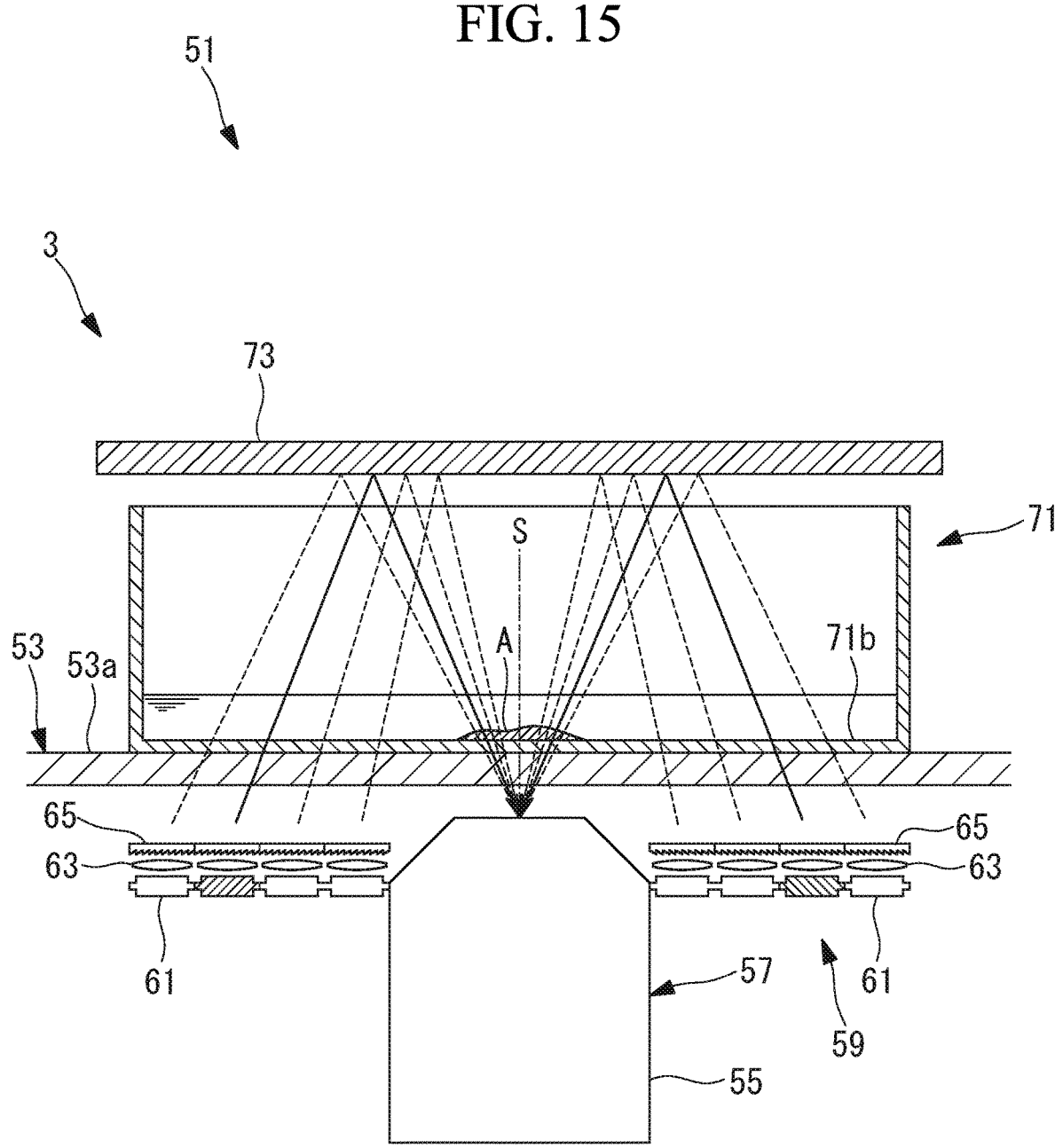
FIG. 15 is a partial longitudinal sectional view illustrating another modification of the culture observation apparatus in FIG. 10.

In addition, in the present embodiment, the cells A are housed in the culture container C having the top plate C2, such as a cell culture flask, and the illumination light is reflected by the inner surface of the top plate C2 of the culture container C; however, the configuration is not limited thereto. For example, as illustrated in FIG. 15, in the case where the cells A are housed in a container 71 having no top plate as a culture container C, such as a petri dish (without a lid), as illustrated in FIG. 15, a reflecting member 73 that is mirror-like may be disposed at a position closing the upper portion opening of the petri dish, and illumination light transmitted through a bottom surface 71b of the container 71 from the bottom upward may be reflected by the reflecting member 73. The reflecting member 73 may be provided so as to be removable at a position above the cells A by direct movement or by swinging.

Figure 16:
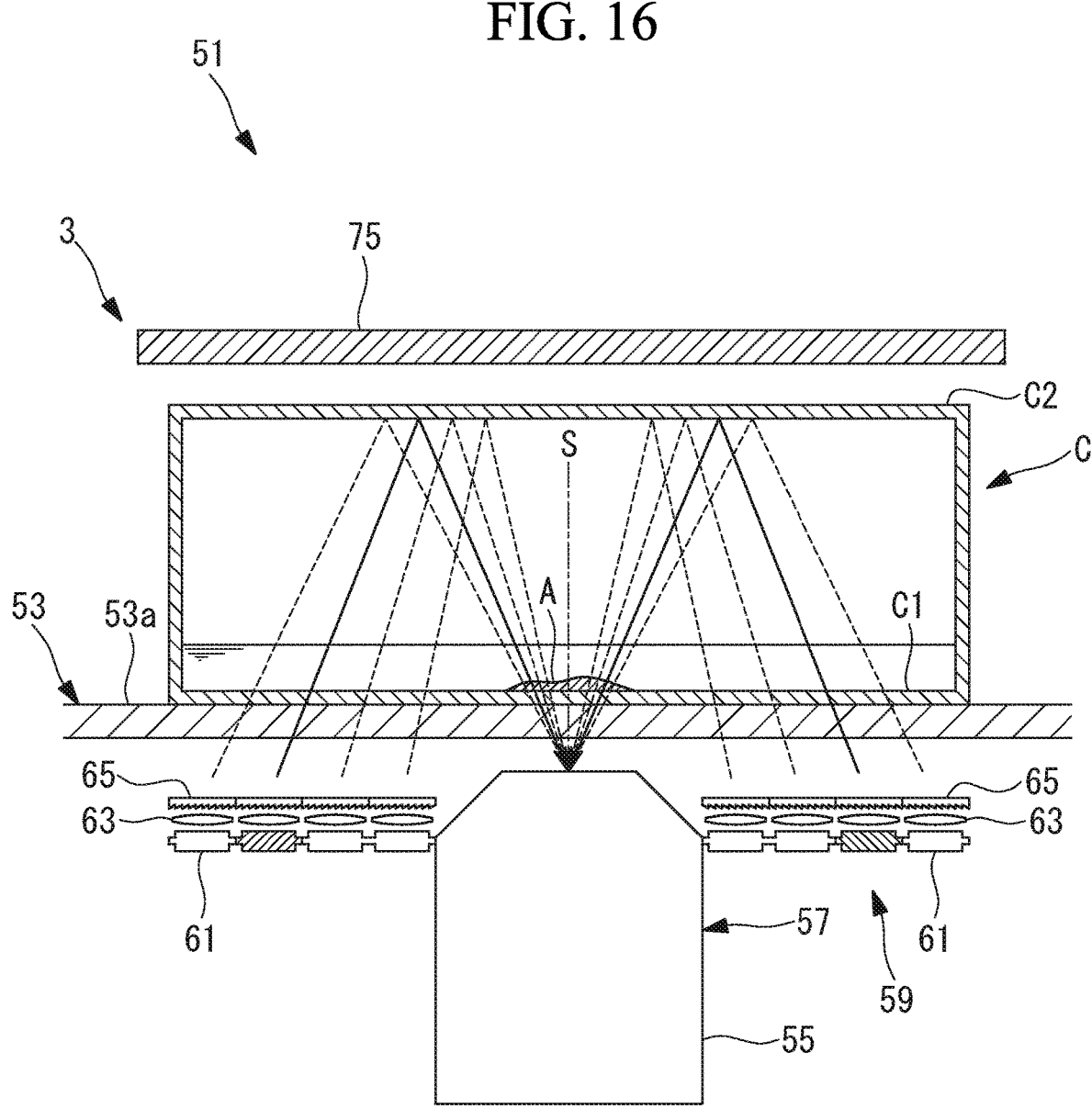
FIG. 16 is a partial longitudinal sectional view illustrating another modification of the culture observation apparatus in FIG. 10.

In addition, in the present embodiment, as illustrated in FIG. 16, a light blocking member 75 composed of a material that blocks light may be provided above the top plate C2 of the culture container C.

By doing so, because external light from the outside is blocked by the light blocking member 75, the external light can be prevented from entering the culture container C from the top plate C2, and observation can be performed efficiently.

Figure 17:
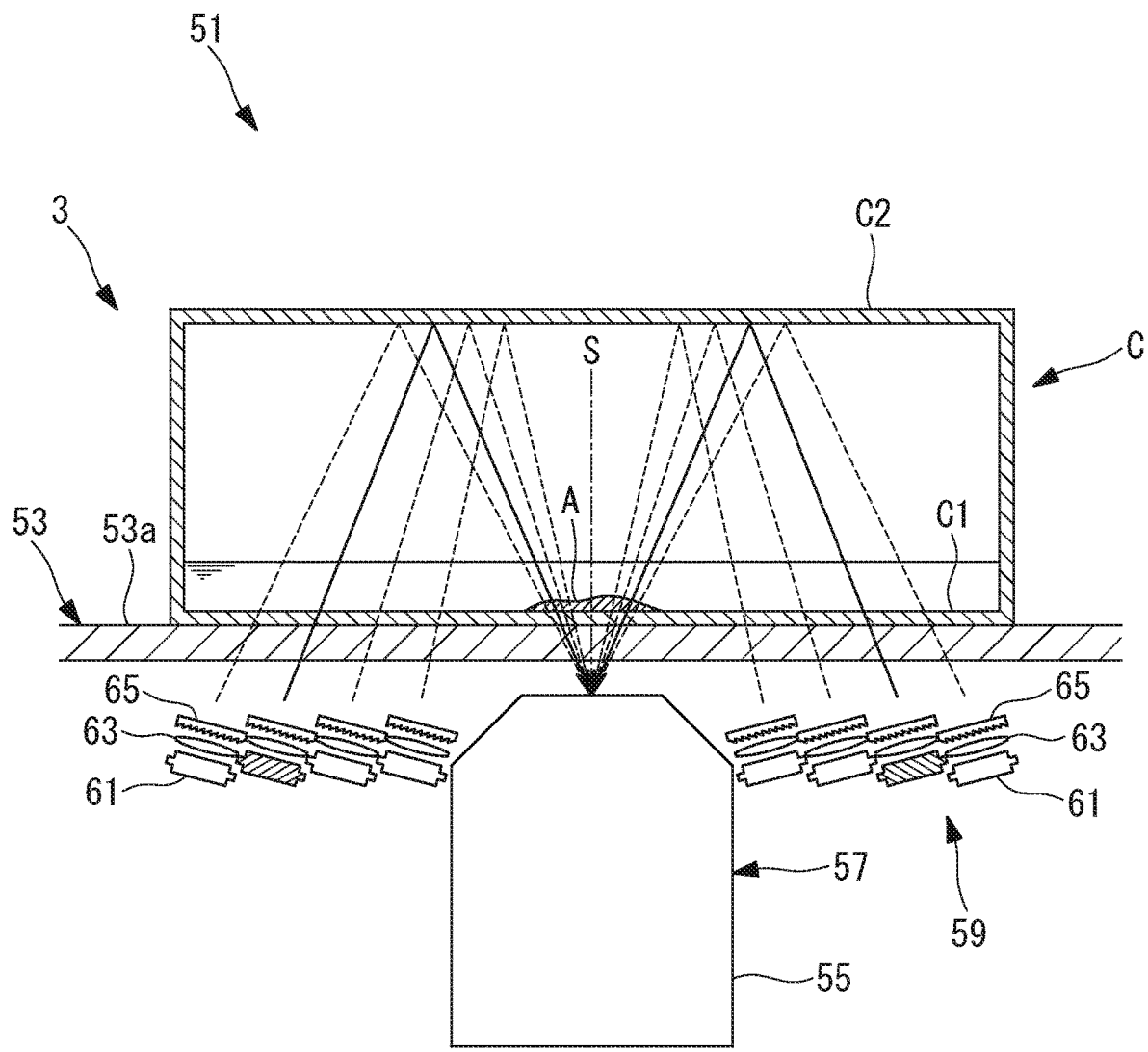
FIG. 17 is a partial longitudinal sectional view illustrating another modification of the culture observation apparatus in FIG. 10.

In addition, in the present embodiment, as the light source unit 59, one in which the LED light sources 61, the collimating lens 63, and the diffusion plate 65 are disposed substantially horizontally along the glass plate 53a is given as an example; however, instead of this, as illustrated in FIG. 17, the LED light sources 61, the collimating lens 63, and the diffusion plate 65 may be disposed so as to be inclined toward the optical axis S.

By doing so, it is possible to suppress loss of illumination light emitted from the LED light sources 61 and to irradiate the cells A with illumination light efficiently.

In addition, in the present embodiment, the light source unit 59 is provided with the diffusion plate 65; however, the diffusion plate 65 need not be provided.

In addition, in the present embodiment, the light source unit 59 is provided with the collimating lens 63; however, the collimating lens 63 need not be provided.

In addition, in the present embodiment, the light source unit 59 includes the collimating lens 63 and the diffusion plate 65; however, the arrangement of the collimating lens 63 and the diffusion plate 65 may be reversed. The collimating lens 63 and the diffusion plate 65 need not be provided.

In addition, in the present embodiment, a configuration in which the light source unit 59 is disposed below the culture container C has been described as an example; however, for example, the light source unit 59 may be disposed above the culture container C, and illumination light may be radiated to the cells A from above.

In addition, in the present embodiment, the imaging optical system 57 may be moved in the X and Y directions by a driving mechanism. In this case, the light source unit 59 may be moved together with the imaging optical system 57 by a driving mechanism.

In addition, in the present embodiment, as the light source unit 59, a configuration in which a plurality of LED light sources (light sources) 61 are disposed at intervals in the circumferential and radial directions around the objective lens 55 has been described as an example; however, a plurality of LED light sources (light sources) may be disposed with a space therebetween only in the circumferential direction. For example, four LED light sources (light sources) may be disposed at intervals of 90° in the circumferential direction. A single LED light source (light source) may be disposed.

Although the embodiments of the present invention have been described above in detail with reference to the drawings, the specific configuration is not limited to the present embodiment and includes design changes and the like within a scope not deviating from the gist of the present invention. For example, the present invention is not limited to application to each of the above-described embodiments and modifications, and may be applied to an embodiment in which these embodiments and modifications are combined as appropriate, and is not particularly limited. In addition, transmission and reception between the transmitting unit 17 and the receiving unit 21 may be wired or wireless.

Fifth Embodiment

Next, a cell culture monitoring system 81 according to a fifth embodiment will be described below with reference to the drawings.

Figure 18:
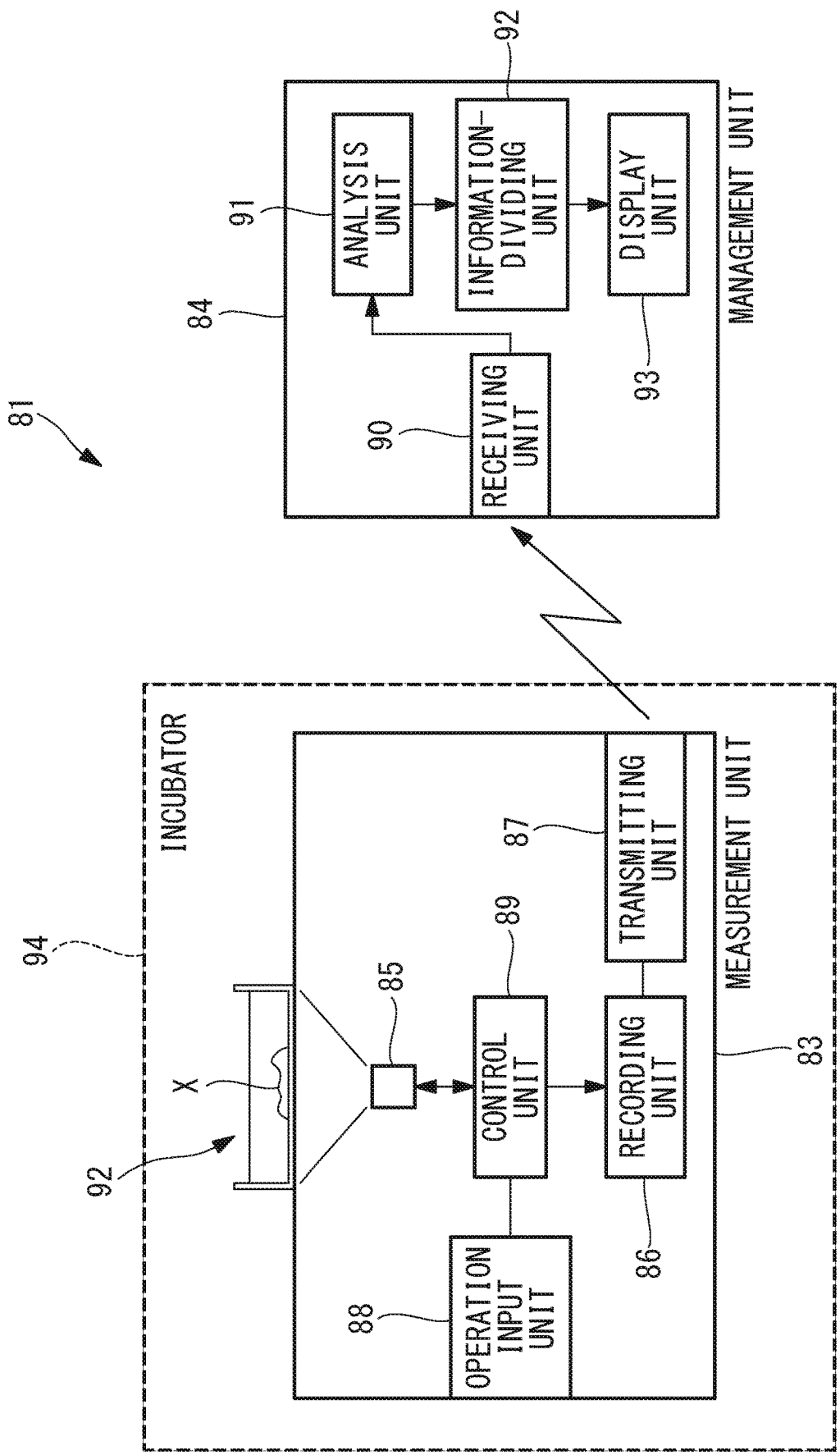
FIG. 18 is an overall configuration diagram illustrating a cell culture monitoring system according to a fifth embodiment.

As illustrated in FIG. 18, the cell culture monitoring system 81 according to the present embodiment includes a measurement unit 83 on which a culture container 82 such as a culture dish or a flask for containing cultured cells X together with a medium is mounted, and a management unit 84 disposed at a position separated from the measurement unit 83.

Figure 19:
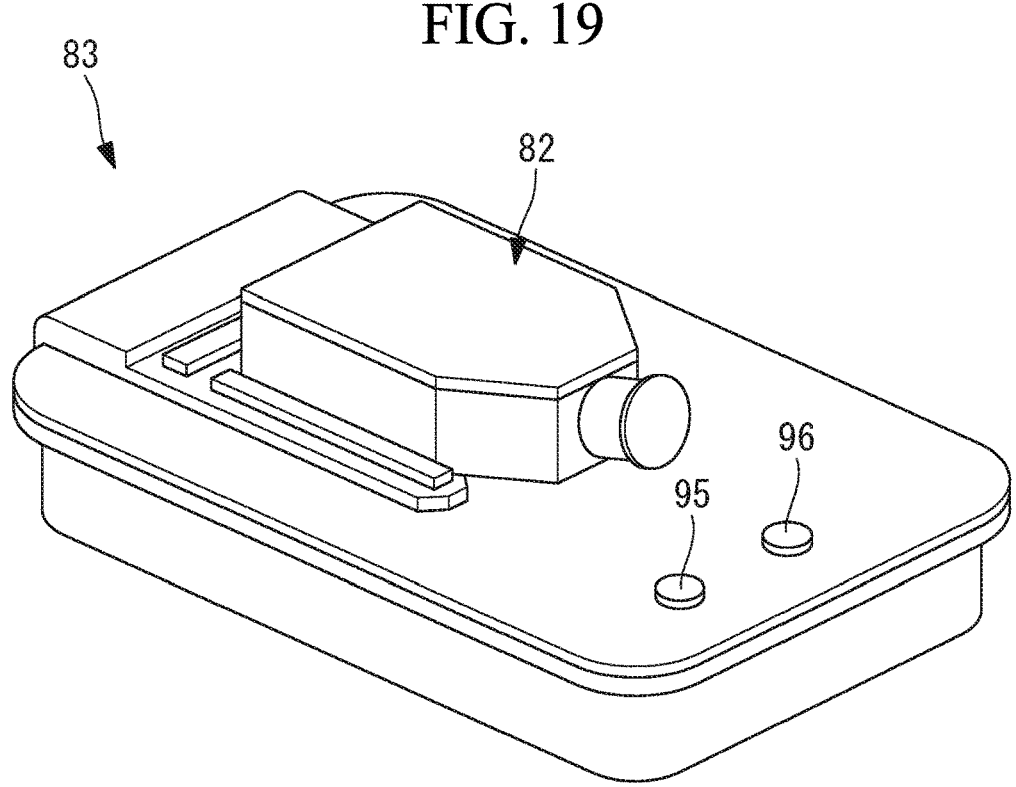
FIG. 19 is a perspective view illustrating an example of a measurement unit provided in the cell culture monitoring system in FIG. 18.

As illustrated in FIG. 19, the measurement unit 83 is a box-shaped casing on which the culture container 82 is mounted and acquires information indicating the state of the cells X adhering to the bottom surface of the culture container 82 and growing.

The measurement unit 83 includes a sensor (cell state acquiring unit) 85 that is housed in an incubator 94 and that acquires information indicating the state of the cells X cultured inside the culture container 82 over time in a state of being kept at a predetermined temperature and humidity, a recording unit 86 that records the information acquired by the sensor 85, a transmitting unit 87 that transmits the information recorded by the recording unit 86 to the management unit 84, an operation input unit 88 that is operated by an operator, and a control unit 99 for controlling the recording unit 86.

As the sensor 85, for example, it is preferable to have a camera that obtains the image of the cells X or an optical sensor such as a light-amount sensor that acquires the amount of light from the cells X; however, an arbitrary sensor capable of acquiring information indicating the state of the cells X can be used. For example, a sensor 85 composed of a camera captures images of the cells X at predetermined time intervals and sends the acquired image information to the control unit 99.

The operation input unit 88 is an input unit for starting, pausing, and resuming observation, and it is possible to adopt an arbitrary input unit such as an operation button.

In the example illustrated in FIG. 19, as an input unit for pausing and resuming, a pause button 95 operated at the time of subculturing and a resume button 96 operated at the time of medium exchange are prepared.

A control unit 89 includes a timer (not illustrated) and a processor (not illustrated) and sends the image information sent from the sensor 85 to the recording unit 86 in association with time.

In addition, when input is performed on the operation input unit 88, the control unit 89 adds a tag to the time at which input of chronological order image information to be sent to the recording unit 86 was performed. As tags, separate tags are added to the pause and resume times for medium change and to the pause and resume times for subculturing, respectively.

Then, when an input for starting or resuming observation is given via the operation input unit 88, the control unit 89 starts recording by the recording unit 86, and when an input for pausing observation is given via the operation input unit 88, the control unit 89 performs control to pause the recording by the recording unit 86 until the next resume input is performed.

The transmitting unit 87, for example, periodically transmits the information recorded in the recording unit 86 by wireless transmission.

The management unit 84 includes a receiving unit 90 that receives information transmitted from the measurement unit 83, an analysis unit 91 that analyzes the received image information, an information-dividing unit 92 that classifies the information outputted from the analysis unit 91, and a display unit 93 that displays the information that has been classified. The analysis unit 91 and the information-dividing unit 92 are constituted by a processor, and the display unit 93 is constituted by a monitor.

By analyzing the image information among the received information, the analysis unit 91 calculates information indicating the culture state, such as the number of cells, cell density and the like, in chronological order. The analysis unit 91 is configured to output to the information-dividing unit 92 the calculated chronological-order information indicating the culture state and tags included in the image information received by the receiving unit 90.

The information-dividing unit 92 classifies the chronological-order information indicating the culture state sent from the analysis unit 91 into a plurality of information sets in accordance with the tags attached at the time of subculture.

Figure 20:
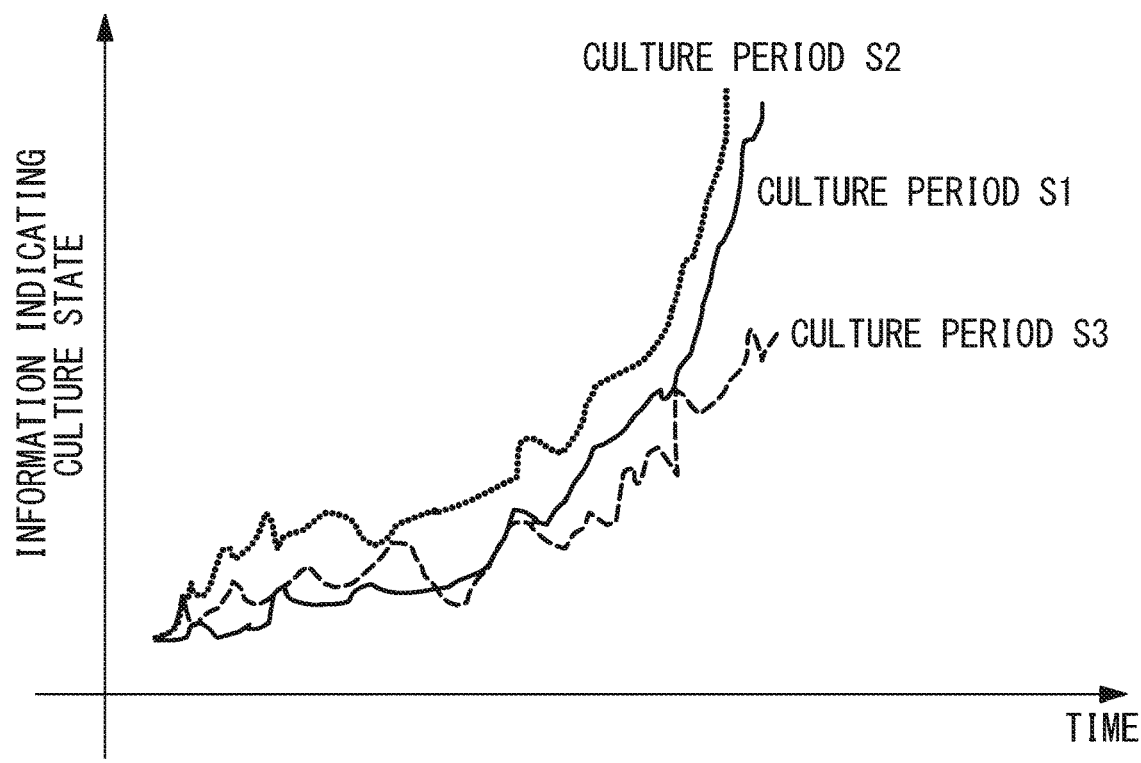
FIG. 20 is a diagram illustrating an example of a graph displayed on a display unit of the cell culture monitoring system in FIG. 18.

Then, the display unit 93 is configured to display a plurality of information sets indicating the culture state classified by the information-dividing unit 92 with their time axes matched. Display of the information with their time axes matched is performed, for example, as illustrated in FIG. 20, by superimposing the information sets on the same coordinates.

The operation of the cell culture monitoring system 81 according to the present embodiment thus configured will be described below.

In order to monitor the culture state of the cells X using the cell culture monitoring system 81 according to the present embodiment, the measurement unit 83 with a culture container housing the cells X and culture medium is disposed in the incubator 94, and observation is started by operating the operation input unit 88.

When the input indicating the start of the observation is given via the operation input unit 88, the control unit 89 controls the recording unit 86 to start recording and adds a tag to the start time. Then, as images of the cells X are periodically acquired, the acquired image information is recorded in the recording unit 86 over time.

When the operator performs a pause input for changing the medium, the control unit 89 adds the tags TC1, TC2, etc. to that time and pauses the recording by the recording unit 86. When the operator performs a resume input after replacing the medium, the control unit 89 adds the tags TD1, TD2, etc. to that time and resumes recording by the recording unit 86.

Replacement work of the medium is carried out multiple times until the subculturing is carried out.

Even when the operator performs a pause input for subculturing, the control unit 89 adds the tags TB1, TB2, etc. to that time and pauses recording by the recording unit 86. When the operator performs a resume input after replacing the medium, the control unit 89 adds the tags TA1, TA2, etc. to that time and resumes recording by the recording unit 86.

The transmitting unit 87 periodically transmits the information recorded in the recording unit 86 or transmits the information according to a request from the management unit 84.

When information is sent from the transmitting unit 87, the receiving unit 90 receives the information and sends it to the analysis unit 91. The analysis unit 91 calculates information indicating the culture state such as cell number and cell density on the basis of the received information indicating the state of cells X.

Figure 21:
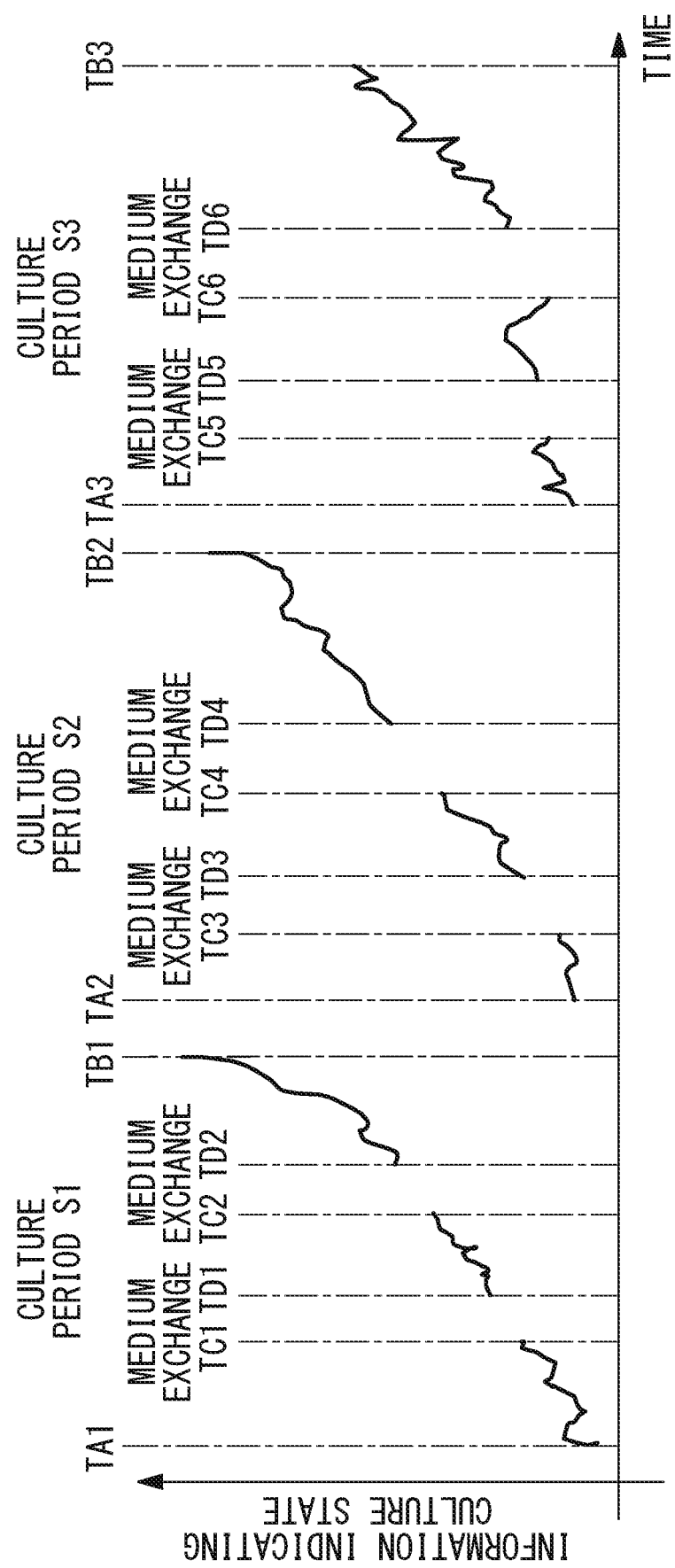
FIG. 21 is a diagram illustrating an example of information indicating a culture state output from the analysis unit of the cell culture monitoring system in FIG. 18.

As a result, in the analysis unit 91, as illustrated in FIG. 21, information indicating the culture state in the chronological order in which tags TA1 to TD6 are respectively attached to the culturing start time, to the pause time for medium exchange, to the resume time after medium exchange, to the pause time for a subculture, and to the resume time after a subculture is generated and output to the information-dividing unit 92. During the periods between pauses and resumption, because the recording by the recording unit 86 is stopped by the control unit 89, since there is no information and the time keeping by the timer of the control unit 89 continues, there are blank periods as illustrated in FIG. 21.

Figure 22:
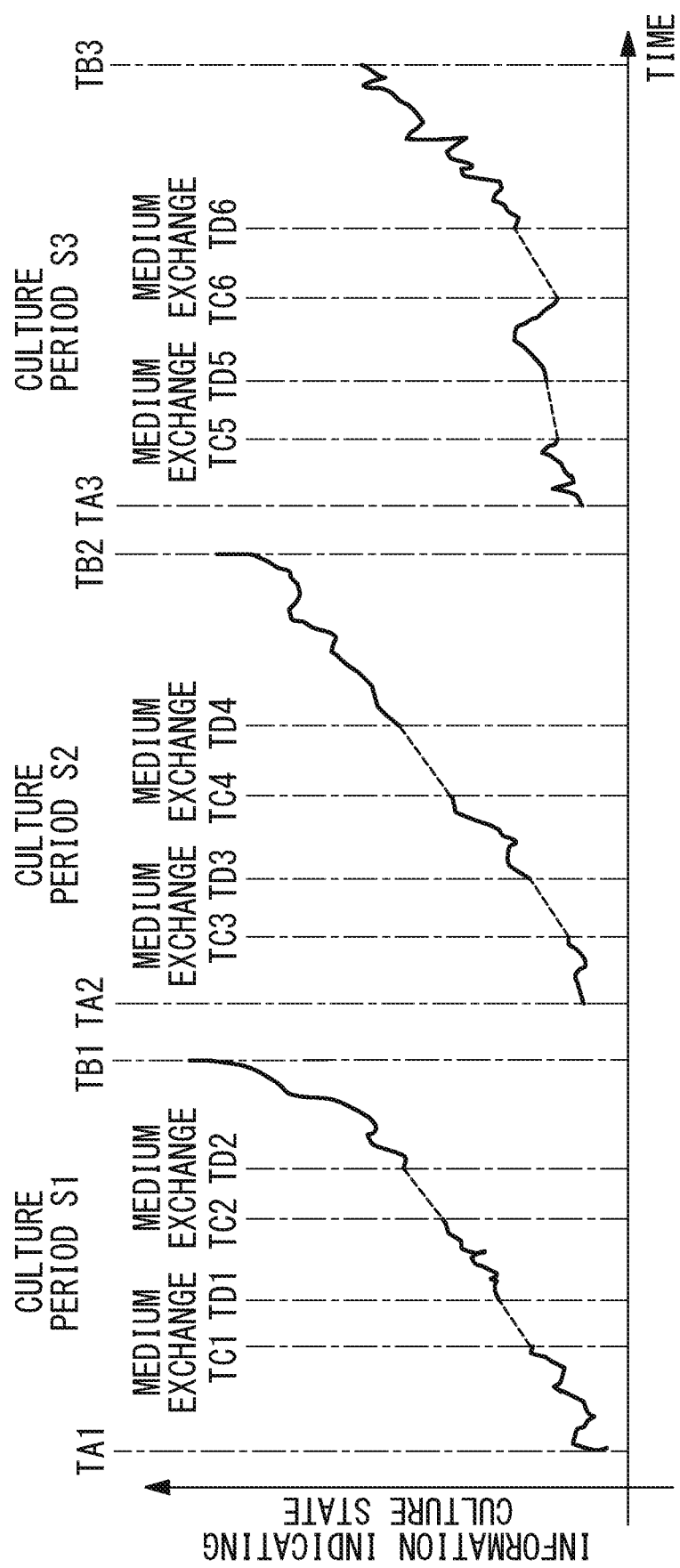

In the analysis unit 91, as illustrated in FIG. 22, the blank periods between pauses and resumption for medium change may be interpolated by an arbitrary method such as linear interpolation.

The information-dividing unit 92, using the tags TA1, TB1, etc. added when the information output from the analysis unit 91 is the observation start time and the pause and resume time for a subculture, classifies the information sets into a plurality of culture periods S1, S2, and S3, and sends them to the display unit 93. In the case where the information output from the analysis unit 91 contains information during culturing, the data from resume-time tags TA1, TA2, etc. after subculturing until the time when the last image is acquired is classified as one information set.

On the display unit 93, as illustrated in FIG. 20, a plurality of sent information sets are displayed as graphs superimposed on the same coordinate axis.

As described above, according to the cell culture monitoring system 81 of the present embodiment, the information indicating the culture states for the culture periods S1, S2, and S3 divided by subculture is indicated by overlapped graphs with the time axes matched, there is an advantage that it is possible to confirm the difference between the culture states of the culture periods S1, S2, and S3 at a glance.

In particular, it is advantageous that, by superimposing graphs containing information during culturing, it is possible to easily determine whether or not the current culture state is appropriate by comparing graphs including information during culturing with other past graphs.

In addition, according to the cell culture monitoring system 81 of the present embodiment, the operation input unit 88 provided in the measurement unit 83 allows the input of operations of starting, pausing, and resuming observation. As a result, operations can be input when the culture container 82 is taken out from the incubator 94 in order to perform medium exchange and subculturing. Because the tags TA1 to TD6 are added to the times at which operations are input, there is an advantage that it is not necessary to perform a special operation for tagging and it is possible to generate a graph that enables easy determination of the suitability of a culture state.

Figure 23:
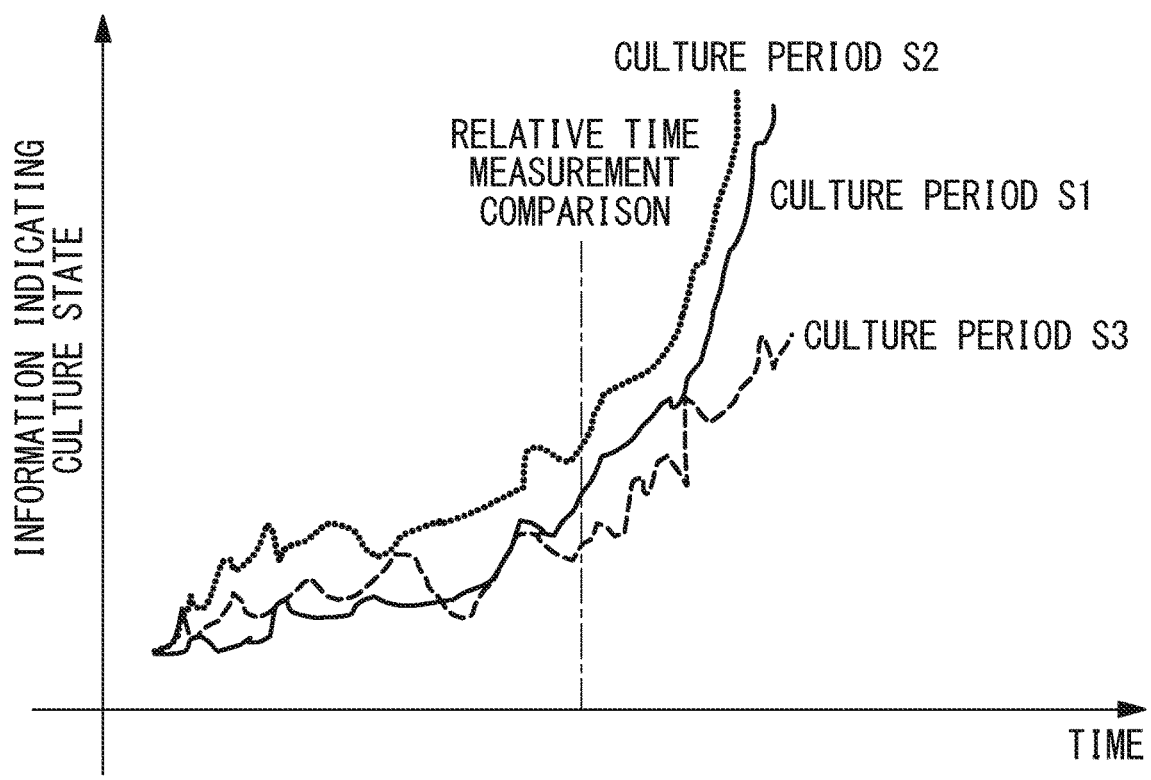
FIG. 23 illustrates a state in which a specific time is specified in the graph in FIG. 20.
Figure 24:
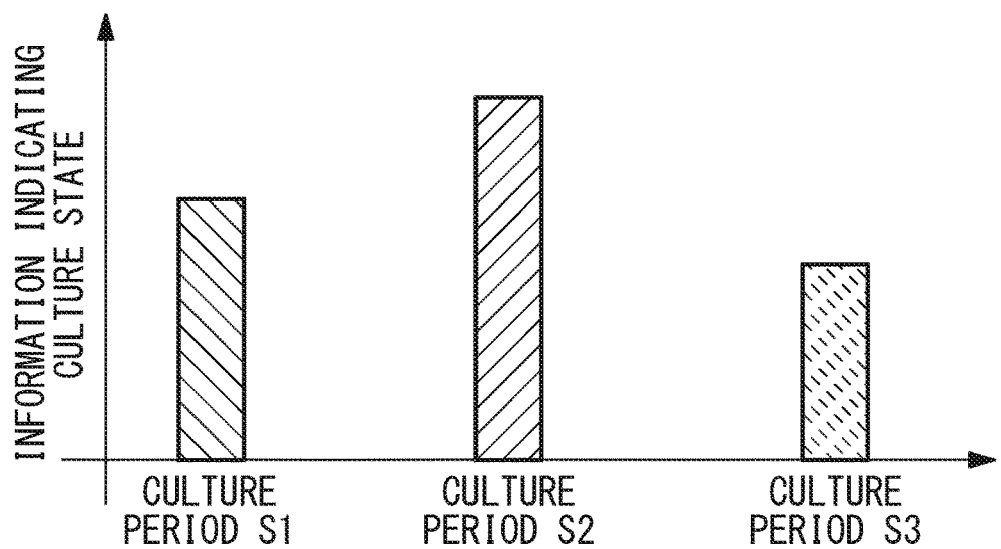
FIG. 24 is a graph comparing information illustrating the culture states for culture periods at the time specified in FIG. 23.

In the present embodiment, the display unit 93 has a GUI, as illustrated in FIG. 23, it is possible to designate a specific time on the displayed graph, and information indicating the culture state at the designated time may be graphically compared as illustrated in FIG. 24.

Figure 25:
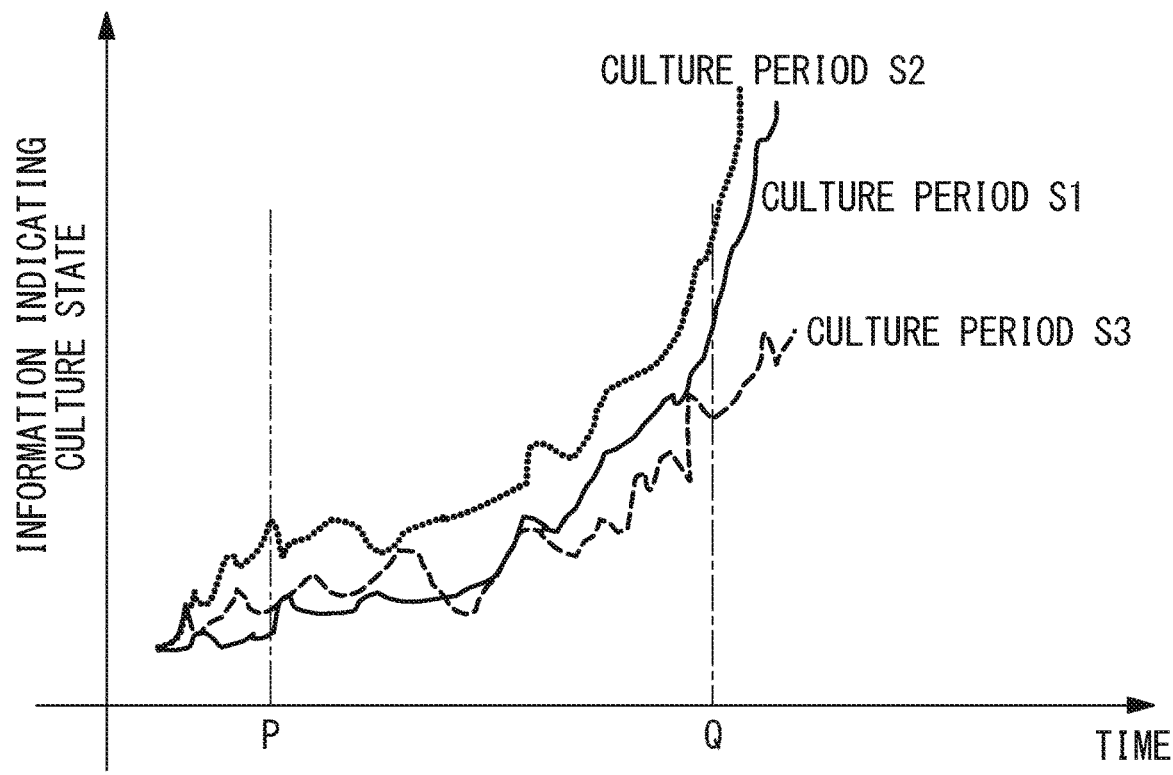
FIG. 25 illustrates a state in which a start point and an end point of a specific period are designated in the graph of FIG. 20.
Figure 26:
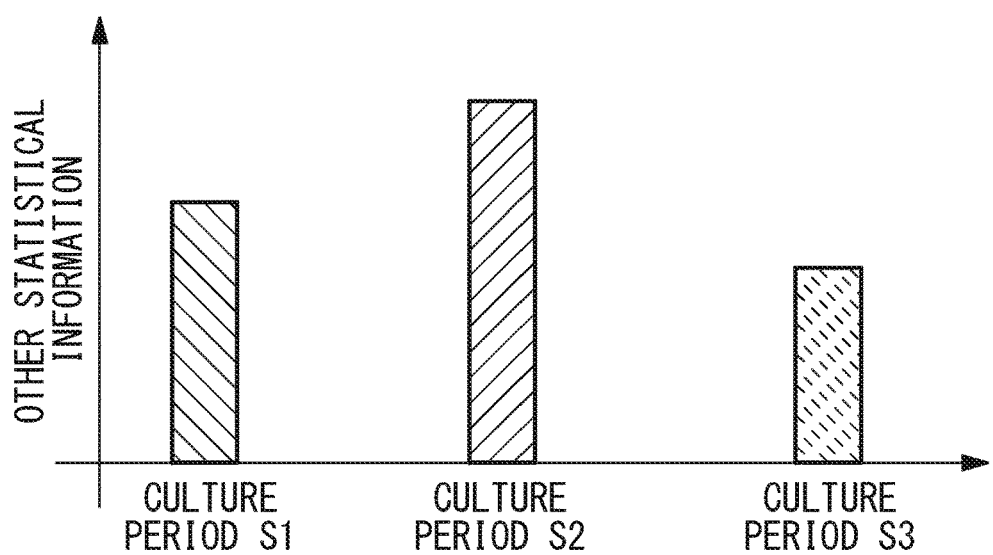
FIG. 26 illustrates comparisons of other statistical information calculated on the basis of information within the time period designated in FIG. 25 for the culture periods.

In addition, as illustrated in FIG. 25, assuming that the start point P and the end point Q of a specific section can be specified in the displayed graph, other statistical information in the section, for example, the proliferation rate, the doubling time or the reciprocal of the doubling time may be calculated and, as illustrated in FIG. 26, the other calculated statistical information can be graphically compared.

Figure 27:
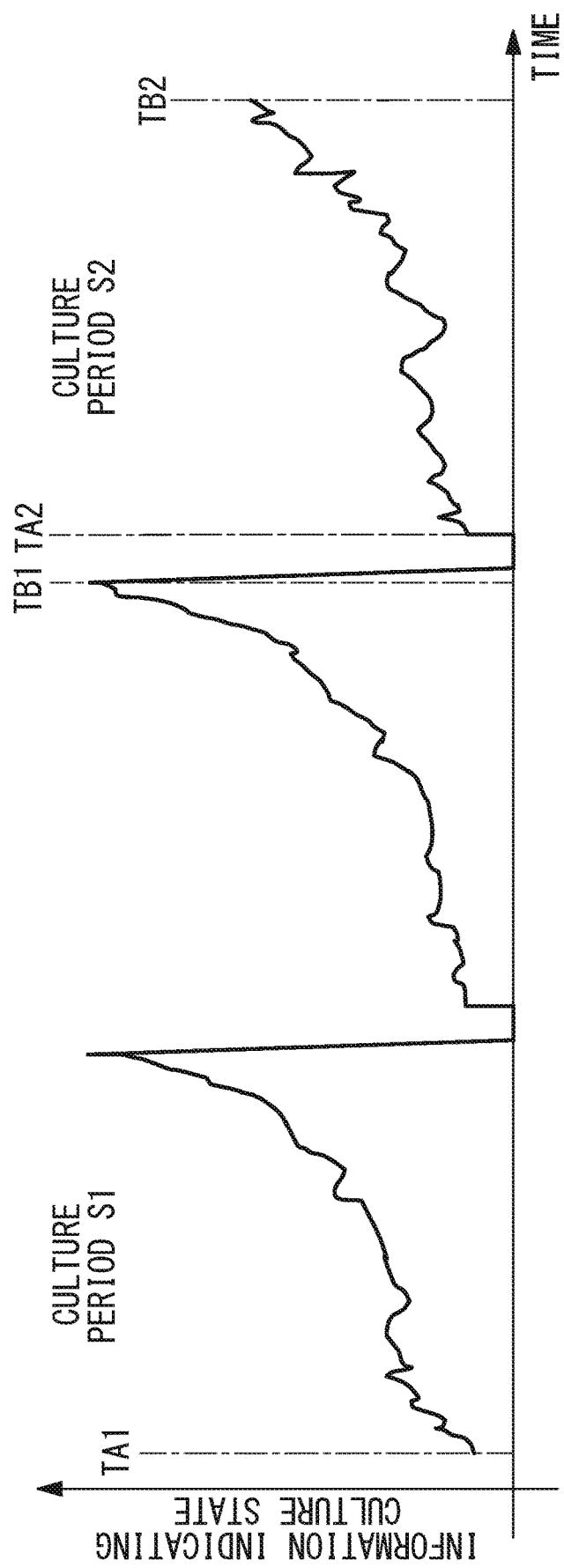
FIG. 27 is a diagram illustrating an example of information output from the analysis unit when neglecting tagging.

In addition, as illustrated in FIG. 27, the tagged chronological-order information output from the analysis unit 91 is displayed on the display unit 93 as is and an information editing unit (not illustrated) may be provided for correction of the positions of the tags TA1, TA2, etc., and TB1, TB2, etc., for addition of tags TA1, TA2, etc., and TB1, TB2, etc., for deletion of tags TA1, TA2, etc., and TB1, TB2, etc., and the like by the operator. In the example illustrated in FIG. 27, the tags are not attached due to reasons such as forgetting to push the pause button 95 and the resume button 96 at the time of subculturing after the first culture period S1 has ended.

Figure 28:
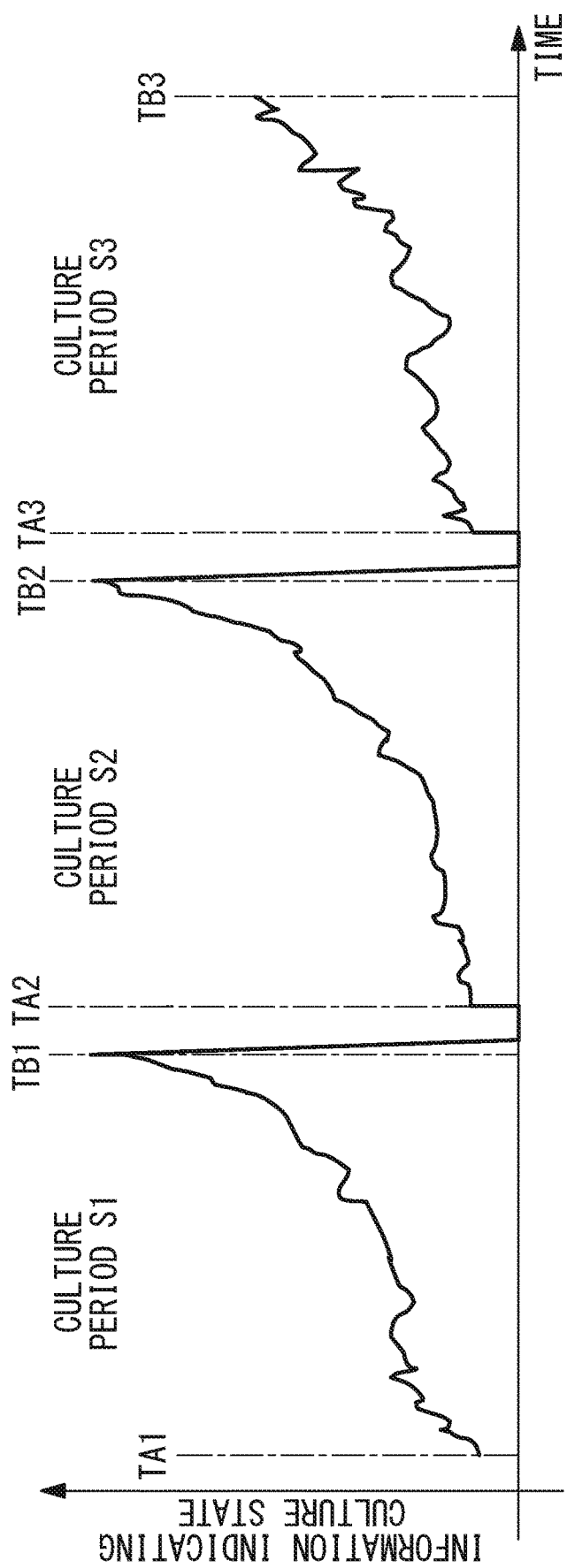
FIG. 28 is a diagram illustrating an example of information in the case where tags are added to the information in FIG. 27.

In such a case, as illustrated in FIG. 28, tags TA1, TA2, etc., and TB1, TB2, etc., may be added at appropriate positions. This makes it possible to prevent the inconvenience that the information indicating the culture state is not properly classified by the information-dividing unit 92 due to the operator forgetting to input operations of pausing and resuming or due to erroneous operation.

In addition, in the present embodiment, the information indicating the culture state is classified by tags added to the observation start time, the pause time, and the resume time by the operator; however, alternatively, the information-dividing unit 92 may automatically classify the information in accordance with the change in the chronological-order information output from the analysis unit 91.

Figure 29:
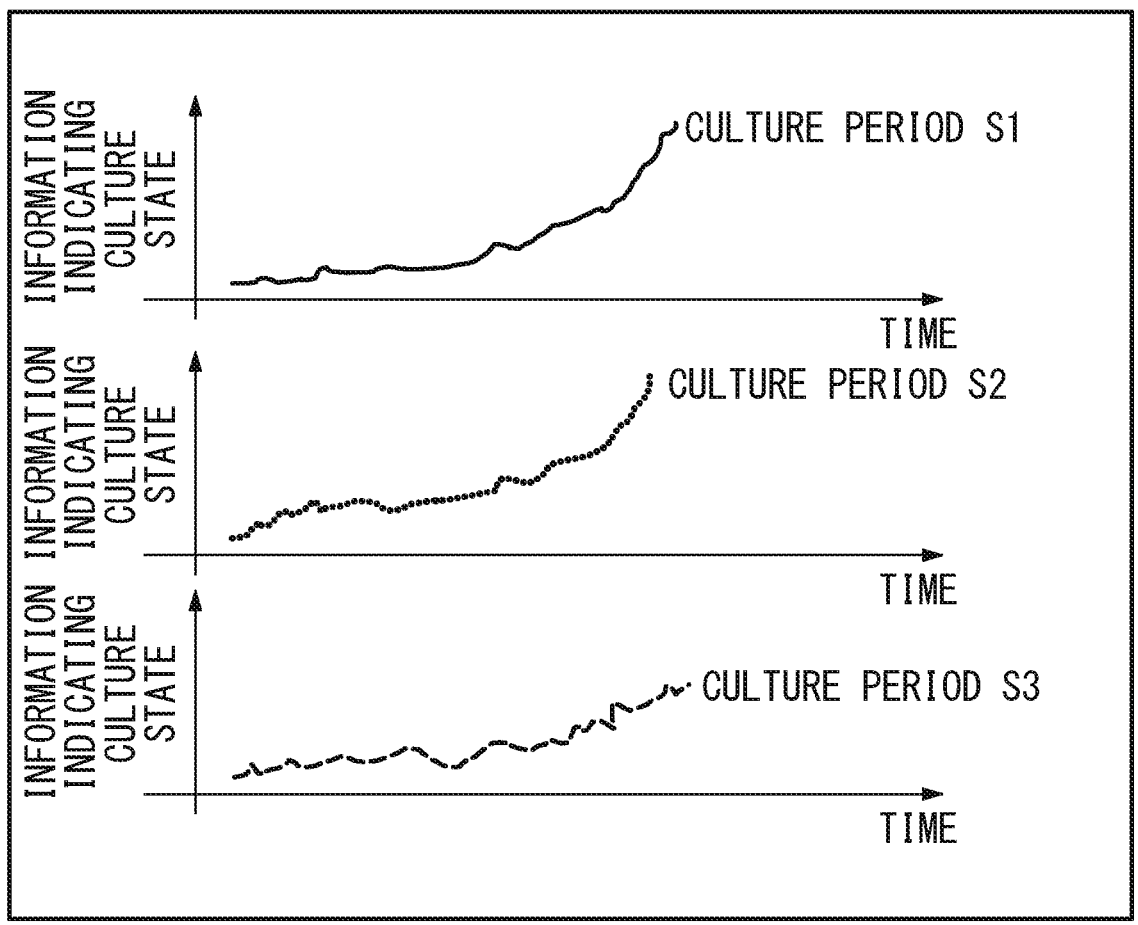
FIG. 29 is a diagram illustrating a modification of a graph displayed on the display unit of the cell culture monitoring system in FIG. 18.

In addition, in the present embodiment, the display of information sets superimposed on the same coordinates has been given as an example of the display of information sets with their time axes matched; however, alternatively, as illustrated in FIG. 29, it is also possible to adopt a configuration in which time axes are matched and displayed side by side.

The fifth embodiment described above can solve the following problems.

To date, in a cell adhesion phase from a time when the cells adhere to the bottom surface of the culture container until the spreading of cells on the bottom surface of the container stops, there is a known cell proliferative capacity evaluation method that evaluates the proliferative capacity of a cell population in a culture container on the basis of the rate at which cells spread, the rate at which cells spread representing a temporal change in a projected area of the cells being observed and measured on the bottom surface of the culture container (refer to, for example, Japanese Unexamined Patent Publication No. 2002-218995).

However, the culturing of the cells is carried out after a plurality of subculturing steps, and JP 2002-218995 does not disclose any evaluation of the culture state in each subculturing step.

Therefore, there was a problem of determining whether or not culture conditions were appropriate for each subculture.

In addition, the following modes are derived from the above-described fifth embodiment.

A mode of the present invention is a cell culture monitoring system including a cell state acquiring unit that acquires information indicating the state of the cells over time, an analysis unit that analyzes information indicating the state of the cells acquired by the cell state acquiring unit and calculates information indicating a culture state, an information-dividing unit for classifying information indicating the culture state calculated by the analysis unit into subcultures, and a display unit that displays, in a manner allowing comparison thereof, the information classified by the information-dividing unit with the time axes matched.

According to this mode, when the state of the cells is acquired over time by the cell state acquiring unit, information indicating the state of the cells is analyzed by the analysis unit, and information indicating the culture state is calculated. Information indicating the calculated culture state is classified into subcultures by the information-dividing unit, and the divided information is displayed, in a manner allowing comparison thereof, on the display unit with the time axes matched. This makes it possible for the operator to compare temporal changes in the culture state displayed on the display unit at a glance for the subcultures and it is easy to judge whether the culture state is appropriate for each subculture.

In the above mode, the information-dividing unit includes an input unit that inputs a signal indicating the start time of culturing and a recording unit for recording that, at the time when the signal is input by the input unit, adds a tag to information indicating a state of the cells acquired over time by the cell state acquiring unit, and the information-dividing unit may classify the information indicating the culture state on the basis of the tags added to the information about the state of the cells over time.

By doing so, when a signal indicating the start time of culturing is input by the input unit, the information is recorded in the recording unit in the form of a tag added to the time of input to the information indicating the state of the cells in chronological order. Then, the information-dividing unit classifies the information indicating the culture state on the basis of tags. As a result, because the information is classified on the basis of the start time of culturing by tags indicating the first start time of culturing and the resume time at the end of subculturing, the time axes can be easily matched for the subcultures, and information that can be compared at a glance can be displayed on the display unit.

In addition, in the above mode, the input unit may be an operation input unit operated when the recording by the recording unit is to be paused and resumed.

By doing so, by the operator operating the operation input unit to stop the recording by the recording unit when the subculturing is started, it is possible to add a tag for classifying information by using a pause operation necessarily carried out at the time of subculturing and it is possible to save the operator labor. By performing classification by using the tags attached to the resume times by the operation, it is possible to easily display, in a manner allowing comparison thereof, the information with the time axes matched.

In addition, in the above-described mode, the display unit may display information classified by the analysis unit side by side.

By doing so, it is possible to display the information classified by the analysis section along the same time axis in a comparable manner at a glance.

In addition, in the above mode, the display unit may superimpose and display information classified by the analysis unit.

By doing so, it is possible to display the information classified by the analysis section along the same time axis in a comparable manner at a glance.

In addition, in the above mode, the information editing unit may include an information editing unit for editing the tags attached to the information indicating the state of the cells recorded in the recording unit.

By doing so, even when the operator erroneously adds a tag by using the input unit or the operation input unit, it is possible to subsequently correct the position of the tag and add or delete a tag by using the information editing unit.

In addition, in this mode, the cell state acquiring unit may be provided in a measurement unit; the analysis unit, the information-dividing unit, and the display unit may be provided in a management unit that is capable of communicating with the measurement unit and that is disposed at a position separated from the measurement unit, and the operation input unit may be provided in the measurement unit.

By doing so, the state of the cells is acquired over time by the cell state acquisition unit provided in the measurement unit, and the acquired information is sent from the measurement unit to the management unit by communication. Then, analysis by the analysis unit and classification of information by the information division unit are performed, and the classified information is displayed, in a manner allowing comparison thereof, with the time axes matched.

Because the operator who has checked the display on the display unit has to access the measurement unit in the case of performing a process such as subculturing or medium exchange on the cells provided in the measurement unit, the operator, at that time, pauses the recording by the recording unit by operating the operation input unit provided in the measurement unit. In addition, after completing the process, the operation input unit is operated again to resume recording by the recording unit. At this time, because tags are added to the information indicating the state of the cells acquired over time and are recorded in the recording unit, it is possible to easily and accurately classify the information by using the information-dividing unit later.

The above-described embodiment also leads to the following invention.

One aspect of the present invention is a cell observation system including an image acquiring unit that acquires images of the inside of a culture container in which cells are cultured, the image acquiring unit acquiring the images over time; an image analysis unit that quantitively analyzes a culture state of the cells cultured in the culture container on the basis of each of the images acquired by the image acquiring unit; a statistical analysis unit that statistically analyzes the data analyzed by the image analysis unit; and a display unit that displays statistical analysis results in the culture container within a plurality of subculture periods obtained by the statistical analysis unit in a manner allowing comparison of the statistical analysis results.

According to this aspect, images of the inside of the culture container are acquired over time by the image acquiring unit, the image analysis unit quantitatively analyzes the culture state of the cells inside the culture container on the basis of each image acquired by the image acquiring unit, and this analyzed data is statistically analyzed by the statistical analysis unit, whereby it is possible to know a change in the number of cells being cultured inside the culture container. Here, when the subculture is repeated, the cells degrade and the proliferative capacity of the degraded cells decreases.

In this case, by using the display unit to display, in a manner allowing comparison thereof, the statistical results obtained by the statistical analysis unit for the culture containers within the plurality of subculture periods, it is possible to view changes in the proliferative capacity of cells during each subculture period without requiring complicated algorithms. As a result, it is possible to evaluate the quality of cells with a simple operation without much effort.

In the above aspect, the display unit may display a proliferation curve representing a temporal change in the number of the cells within each of the plurality of subculture periods.

When the cells proliferate and the proliferative capacity decreases due to repeated subculturing, the rising curve of the proliferation curve becomes gentle. With this configuration, it is possible to grasp a change in the proliferative capacity of the cells for each subculture period at a glance by the slope of the proliferation curve displayed by the display unit.

In the above aspect, the display unit may superimpose and display the proliferation curve of each of the plurality of subculture periods.

With this configuration, it is possible to grasp differences in the proliferative capacities of the cells for a plurality of subculture periods of interest at a glance.

In the above aspect, a comparing unit may be provided that compares temporal changes in the number of cells for each of the plurality of subculture periods and outputs a change in a proliferation rates of the cells.

With this configuration, the comparing unit can easily grasp a change in the proliferative capacity of the cells for each subculture period and it is possible to save the user the trouble of comparison.

In the above aspect, a quality evaluation unit may be provided that evaluates quality of the cells on the basis of a proliferation rate of the cells in the plurality of subculture periods.

With this configuration, it is possible for the quality evaluation unit to easily divide the cells into cells of a subculture period having a desired quality and cells of a subculture period having no desired quality.

REFERENCE SIGNS LIST 1, 31, 41, 51 cell observation system
3 culture observation apparatus (image acquisition unit
7 monitor (display part)
23 cell analysis section (image analysis section, statistical analysis section, comparison section, quality evaluation section)
A, X cells
C culture container
81 cell culture monitoring system
83 measurement unit
84 management unit
85 sensor (cell state acquisition unit)
86 recording section
88 operation input unit (input unit)
91 analysis unit
92 information division unit
93 display unit

The invention claimed is:

1. A cell observation system comprising:
an incubator inside which an imaging sensor, a transmitter, and a culture container are disposed, cells being cultured in the culture container; and
a processor disposed outside the incubator;
wherein the imaging sensor acquires images of the inside of the culture container over time in a succession of culture processes,
the transmitter transmits the acquired images to outside the incubator,
the processor is configured to:
receive the transmitted images;
quantitatively analyze a culture state of the cells cultured in the culture container on the basis of each of the received images;
statistically analyze the quantitatively analyzed data, and
display statistical analysis results in the culture container within a plurality of subculture periods obtained by the processor in a manner allowing comparison of the statistical analysis results,
a period from after a subculture operation has been performed or from after culturing has been started to the next subculture operation is defined as one subculture period of the plurality of subculture periods, and
the plurality of subculture periods comprise at least two subculture periods obtained as a result of repeating the subculture operation in the succession of the culture processes.

2. The cell observation system according to claim 1, wherein the processor displays a proliferation curve of the cells within each of the plurality of subculture periods.

3. The cell observation system according to claim 2, wherein the processor superimposes and displays the proliferation curve of each of the plurality of subculture periods.

4. The cell observation system according to claim 2, wherein the processor compares the proliferation curve of the cells for each of the plurality of subculture periods and outputs a change in a proliferation rate of the cells.

5. The cell observation system according to claim 1, wherein the processor evaluates a quality of the cells on the basis of a proliferation rate of the cells in the plurality of subculture periods.

* * * * *